United States Patent [19]

DeVries et al.

[11] Patent Number: 4,968,790

[45] Date of Patent: Nov. 6, 1990

[54] ANTIDIABETIC PHOSPHATES

[75] Inventors: Vern G. DeVries, Ridgewood; Thomas H. Claus, Montvale, both of N.J.; Middleton B. Floyd, Jr., Suffern; Semiramis Ayral-Kaloustian, Tarrytown, both of N.Y.

[73] Assignee: American Cyanamid Company, Stamford, Conn.

[21] Appl. No.: 264,480

[22] Filed: Oct. 28, 1988

Related U.S. Application Data

[63] Continuation-in-part of Ser. No. 232,332, Aug. 12, 1988, abandoned.

[51] Int. Cl.$^5$ .................... C07H 13/00; C08B 37/00; A01C 1/00; A61K 31/00
[52] U.S. Cl. .................... 536/117; 536/119; 536/1.1; 536/4.1; 514/866; 514/884; 47/58
[58] Field of Search ................ 536/117, 119, 1.1, 4.1; 47/58; 514/866, 884

[56] References Cited

U.S. PATENT DOCUMENTS 4,745,185 5/1988 Maryanoff et al. ................ 536/117

OTHER PUBLICATIONS

The British Drug Houses Ltd., B. D. H. Laboratory Chemical Division, Poole, England, "Sugar Phosphates and Some Closely Related Substances", Mar. 1958, p. 5.
Brigl et al., Berichte, 66, 325–330 (1933).
Rabinsohn et al., J. Org. Chem., 32, 3452–3457 (1967).
Koerner et al., Carbohydrate Res., 59, 403–416 (1977).
Pilkis et al., J. Biol. Chem., 256, 3171–3174 (1981).
Voll et al., Carbohydrate Res., 95, 145–154 (1981).
Otero et al., Carbohydrate Res., 128, 79–86 (1984).
McClard et al., Arch. Biochem. & Biophys., 245, 282–286 (1986).
Meuwly, Helv. Chim. Acta, 69, 751–760 (1986).
Nicotra et al., J. Org. Chem., 52, 5627–5630 (1987).
Reitz et al., Tetrahedron Letters, 26, 3915–3918 (1985).
Maryanoff et al., Carbohydate Res., 171, 259–278 (1987).

Primary Examiner—Ronald W. Griffin
Assistant Examiner—Everett White
Attorney, Agent, or Firm—Alan M. Gordon

[57] ABSTRACT

Phosphates are disclosed which stimulate the enzyme fructose-1,6-bisphosphatase and inhibit the enzyme 6-phosphofructo-1-kinase, thereby lowering glucose levels in mammals. These phosphates may thus be used to treat hyperglycemia and/or diabetes. Processes for the synthesis of the phosphates are also disclosed.

42 Claims, No Drawings

ANTIDIABETIC PHOSPHATES

BACKGROUND OF THE INVENTION

This application is a continuation-in-part of Ser. No. 232,332, now abandoned, filed Aug. 12, 1988.

This invention relates to novel organic compounds which are useful as pharmaceutical agents. The novel compounds of this invention modulate the activity of enzymes which control the processes of glycolysis and gluconeogenesis, two processes which help to regulate blood glucose levels in mammals. As such, the compounds of the present invention are useful for treating hyperglycemia and/or diabetes in warm-blooded animals. This invention also relates to methods for treating hyperglycemia and/or diabetes in mammals in need of such treatment, to pharmaceutical compositions for the utilization of these novel compounds in the treatment of hyperglycemia and/or diabetes and to processes for the chemical syntheses of these compounds.

The disease diabetes mellitus, commonly referred to as diabetes, is characterized by metabolic defects in the production and disposal of glucose. The result of these defects is the inability to maintain appropriate blood glucose (or blood sugar) levels. Treatments of diabetes have commonly employed the administration of exogenous insulin, the oral administration of drugs, or the use of dietary therapy. Initially, it was believed that the hyperglycemia observed in diabetics was simply the result of a deficiency in the supply of insulin, the principal hormone which controls glucose metabolism. As a result, research focused on the source of insulin production, the beta cells of the pancreas, and pharmaceutical agents which stimulated these cells to release insulin were developed.

Although it is true that a deficiency in insulin production can produce hyperglycemia, it has now been recognized that a variety of defects in metabolic processes can play a major role in the control of blood glucose levels. Metabolic processes which are important in this regard include glycolysis (the metabolic degradation of glucose to lactic acid), gluconeogenesis (the metabolic process by which endogenous synthesis of glucose from lactic acid occurs), glycogenolysis (the metabolic process by which glucose is released from stored glycogen), and insulin-stimulated glucose uptake (the metabolic process by which peripheral tissues acquire glucose as an energy source). Defects in any or all of these metabolic processes have significant effects on the maintenance of appropriate blood glucose levels.

In Type I diabetes, also called juvenile-onset or insulin-dependent diabetes, a deficiency in insulin production is the major cause of hyperglycemia. However, the majority of diabetics suffer from a form of the disease referred to as Type II, also called maturity-onset or noninsulin-dependent diabetes. In most Type II diabetics, basal insulin levels are normal or even elevated; in spite of this, transient or continuous elevations in blood glucose levels occur. In such disease states, the metabolic processes mentioned above, which normally function to provide exquisite control over blood glucose levels, are operating in an aberrant manner. Thus, a pharmaceutical agent capable of regulating these processes would be useful in restoring normal metabolic control of blood sugar levels.

Two of the above-described metabolic processes which are vitally important to glucose homeostasis are glycolysis and gluconeogenesis. In the process called glycolysis, glucose is converted in a series of enzymatically catalyzed transformations to lactic acid. In the process called gluconeogenesis, glucose is synthesized from lactic acid in another series of enzymatically catalyzed transformations. It is well known that proper regulation of these two metabolic processes is essential for the maintenance of appropriate blood glucose levels.

In recent years, research has resulted in the discovery of a natural product, beta-D-fructose-2,6-bisphosphate (Pilkis et al., *J. Biol. Chem.*, 256, 3171–3174 (1981)), which has now been demonstrated to be an important regulator of both glycolysis and gluconeogenesis. Beta-D-fructose-2,6-bisphosphate exerts its regulatory action on these metabolic processes by specifically modulating the activity of a key enzyme involved in each of these processes. First, beta-D-fructose-2,6-bisphosphate promotes glycolysis by stimulating the enzyme 6-phosphofructo-1-kinase, which catalyzes the conversion of fructose-6-phosphate to fructose-1,6-bisphosphate. Second, beta-D-fructose-2, 6-bisphosphate attenuates gluconeogenesis by inhibiting the enzyme fructose-1,6-bisphosphatase, which catalyzes the conversion of fructose-1,6-bisphosphate to fructose-6-phosphate. Either or both of these regulatory actions serve to reduce glucose levels, the former by promoting the metabolic degradation of glucose and the latter by attenuating the endogenous synthesis of glucose. Thus, the net result of the regulatory action of beta-D-fructose-2,6-bisphosphate is a lowering of glucose levels, the exact result desired in the treatment of hyperglycemic and/or diabetic states.

It has now been found that the novel organic compounds of the present invention exert regulatory actions on the key enzymes of the glycolytic and gluconeogenic processes in the same manner as the natural product, beta-D-fructose-2,6-bisphosphate. The novel compounds are more resistant to enzymatic or hydrolytic degradation than the natural product, which has a labile acetal phosphate group. The novel compounds are stimulators of the enzyme 6-phosphofructo-1-kinase and inhibitors of the enzyme fructose-1,6-bis-phosphatase; the net result of these actions being the lowering of glucose levels. As such, they are useful for the treatment of hyperglycemic and/or diabetic states in mammals.

SUMMARY OF THE INVENTION

This invention relates to novel organic compounds of Formula I:

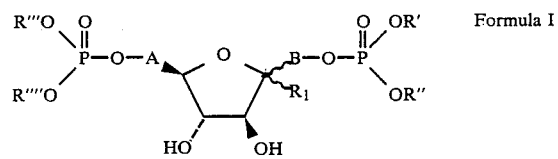

Formula I wherein A and B are selected independently of each other from the group consisting of $C_1$ to $C_4$ alkylene and $C_2$ to $C_4$ hydroxyalkylene; $R_1$ is selected from the group consisting of hydrogen, $C_1$ to $C_4$ alkyl, $C_1$ to $C_4$ hydroxyalkyl, $C_2$ to $C_4$ dihydroxyalkyl, $C_3$ to $C_4$ trihydroxyalkyl and $C_4$ tetrahydroxyalkyl; $R'$, $R''$, $R'''$ and $R''''$ are selected independently from the group consisting of hydrogen, $C_1$ to $C_{18}$ alkyl, $C_3$ to $C_6$ cycloalkyl, phenyl, isoalkyl ($C_3$–$C_8$), $Cl_3CCH_2$—, $CH_2$=$CHCH_2$—, $ZCH_2CH_2$—[where Z is $SO_2R_2$, $SR_2$, $OR_2$ or $Si(R_2)_3$, and $R_2$ is alkyl ($C_1$–$C_3$)], halo,

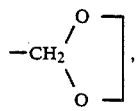

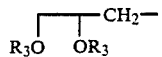

[where $R_3$ is hydrogen, alkyl ($C_1$-$C_{18}$) and $R_3$-$R_3$ is alkylene or acetal],

(where $R_4$ is hydrogen or methyl),

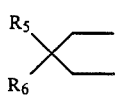

[where when $R_5=R_6$, they are both hydrogen, fluoro or alkyl ($C_1$-$C_4$), $R_5=$hydrogen, $R_6=$fluoro, hydroxy or $OR_7$ [where $R_7=$alkyl ($C_1$-$C_6$), cycloalkyl ($C_3$-$C_6$) or aryl]],

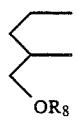

where $R_8=$hydrogen or alkyl ($C_1$-$C_{18}$)],

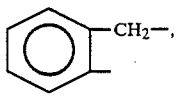

phenylmethyl, substituted phenylmethyl wherein the substituents are selected from alkyl ($C_1$-$C_{18}$), alkoxy ($C_1$-$C_6$), $NO_2$ and halogen, and mono- and disubstituted phenyl wherein the substituents are selected from alkyl ($C_1$-$C_{18}$), alkoxy ($C_1$-$C_6$), $NO_2$ and halogen; with the proviso that when A and B are both —$CH_2$—, then $R_1$ may not be hydrogen; and, when any one or more of R', R'', R''' or R'''' are hydrogen, the pharmacologically acceptable salts thereof.

This invention is also concerned with novel organic compounds of Formula II:

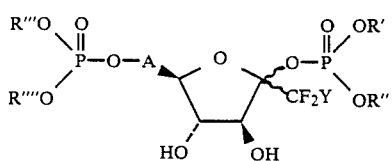

Formula II wherein A, R', R'', R''' and R'''' are as described above in Formula I and Y is selected from the group consisting of hydrogen, $COOR_9$ and $CH_2OH$, where $R_9$ is hydrogen or a salt thereof, or alkyl ($C_1$-$C_6$)

This invention further relates to novel organic compounds of Formula III:

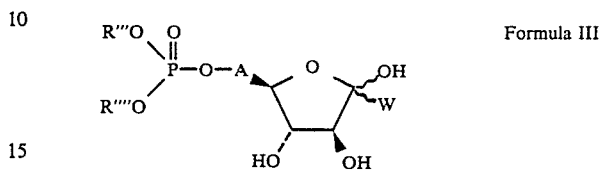

Formula III wherein A is as described above in Formula I; R''' and R'''' are as described in Formula I or are —$CH_2CH_2N^+(C_3)_3$,

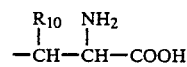

[where $R_{10}$ is hydrogen or $C_1$ to $C_3$ alkyl] and

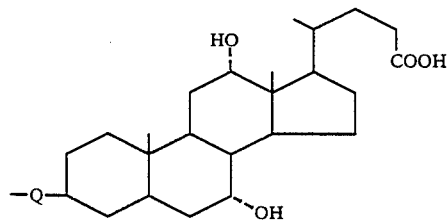

[where Q is a bond, —$(CH_2)_n$— or —$(CH_2)_n$—O— and n=1-]; and W is selected from the group consisting of —$CFH_2$, —$CF_2H$, —$CF_3$, —$CF_2CH_2OH$, —$CF_2COOH$, COOH and —$COOCH_3$, and the pharmacologically acceptable salts thereof.

This invention is further concerned with methods of treating hyperglycemia and/or diabetes in mammals in need of such treatment and to pharmaceutical compositions of matter employing compounds of the above Formula I (without the proviso) and the above Formula II.

DETAILED DESCRIPTION OF THE INVENTION

Compounds of the present invention may be prepared according to the following flowcharts. In these flowcharts, the phenyl group

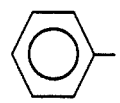

is abbreviated Ph.

Flowchart A
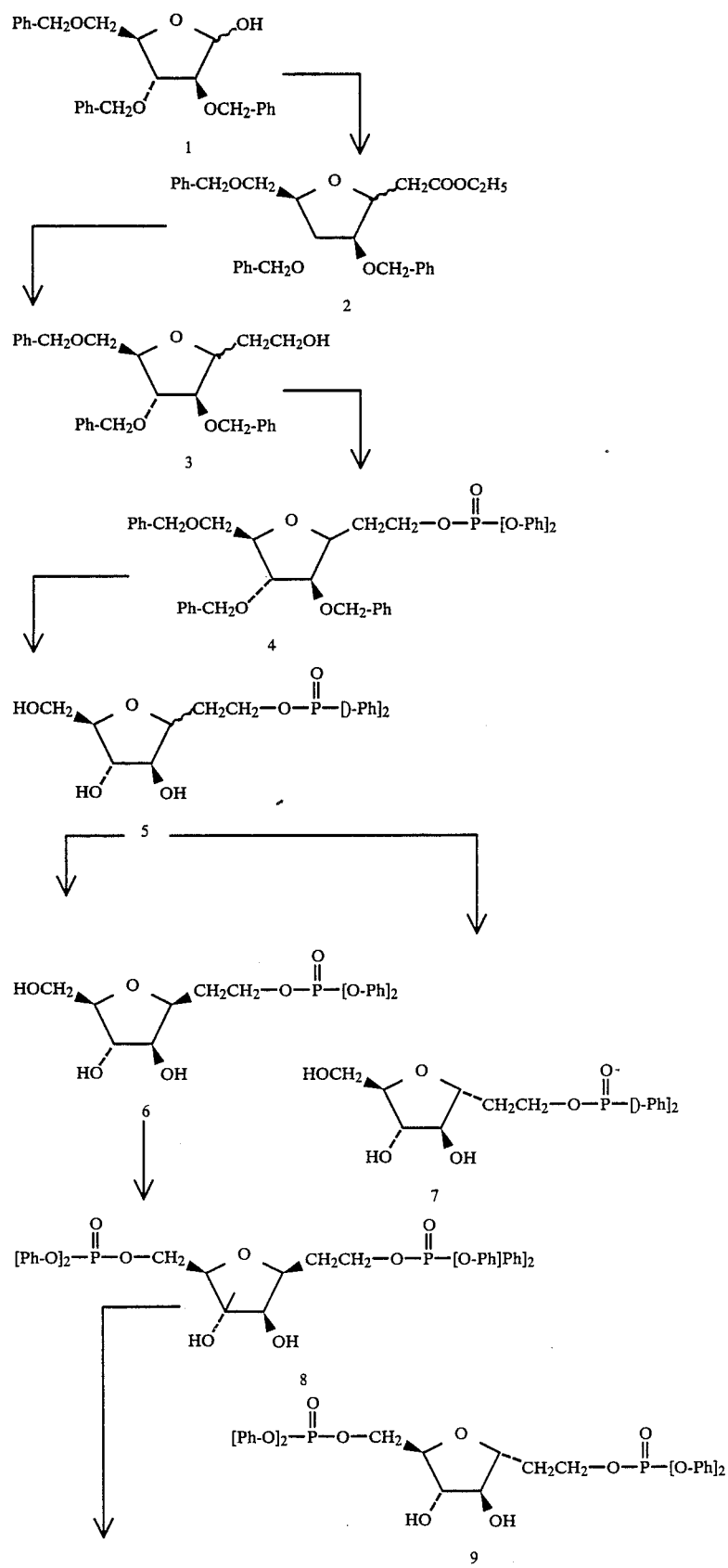

Flowchart A

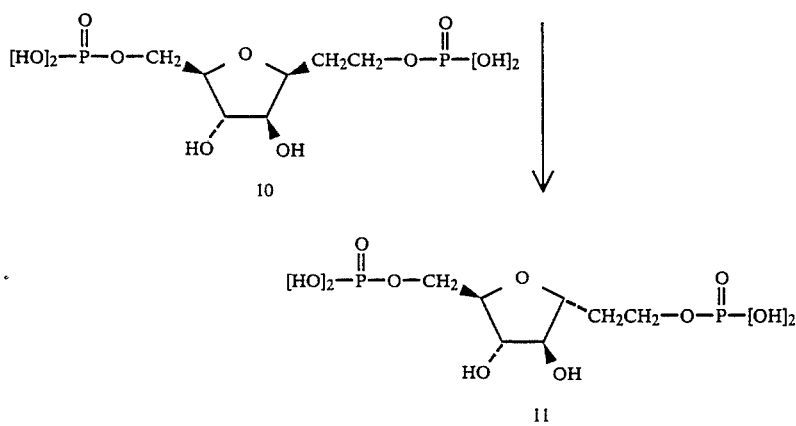

In accordance with Flowchart A, 2,3,5-tris-O-(phenylmethyl)-D-arabinofuranose 1 is reacted with a reagent composed of sodium hydride, dimethoxyethane and triethylphosphonoacetate, giving 2,3-dideoxy-4,5,7-tris-O-(phenylmethyl)-D-arabino-3-heptulo-3,6-furanosonic acid, ethyl ester 2. Compound 2 in ether solution is then added dropwise to lithium aluminum hydride in ether under an inert atmosphere, followed by treatment with sodium sulfate, giving a mixture of 3,6-anhydro-2-deoxy-4,5,7-tris-O-(phenylmethyl)-D-glucoheptitol and 2,5-anhydro-6-deoxy-1,3,4-tris-O-(phenylmethyl)-D-manno-heptitol 3.

The mixture of compound 3 is treated with diphenylphosphorochloridate in pyridine at 0° to −10° C., giving a mixture of 3,6-anhydro-2-deoxy-4,5,7-tris-O-(phenylmethyl)-D-gluco-heptitol, 1-(diphenyl phosphate) and 3,6-anhydro-2-deoxy-4,5,7-tris-O-(phenylmethyl)-D-manno-heptitol, 1-(diphenyl phosphate) 4. Using other substituted phosphoro chloridates in the above reaction will produce the corresponding esters analogous to 4, where the R', R", R''', R'''' groups may be chosen independently from each other from any of the a through t groups in Table I.

The mixture 4 is then hydrogenated in methanol and acetic acid over palladium on carbon, giving a mixture 5 which is separated by chromatography into components 3,6-anhydro-2-deoxy-D-gluco-heptitol, 1-(diphenyl p hosphate) 6 and the corresponding-D-manno derivative 7.

The gluco 6 and manno 7 components are then treated separately but identically as follows: Each is reacted with diphenyl phosphorochloridate in pyridine at reduced temperature, giving (from 6) the product of Formula I where R', R", R''' and R'''' are each phenyl, 3,6-anhydro-2-deoxy-D-gluco-heptitol, 1,7-bis (diphenyl phosphate) 8 and from 7 the corresponding D-manno derivative 9. Using other substituted phosphorochloridates in the above reaction will produce the corresponding esters of Formula I, where R', R", R''' and R'''' may be selected independently from each other from any of the groups a through t in Table I.

The esters 8 and 9 may then be individually hydrogenated in methanol over platinum oxide, giving (from 8) the product of Formula I where R', R", R''' and R'''' are hydrogen, 3,6-anhydro-2-deoxy-D-gluco-heptitol, 1,7-bis (dihydrogen phosphate) 10 and (from 9) 3,6-anhydro-2-deoxy-D-manno-heptitol, 1,7-bis (dihydrogen phosphate) 11.

Flowchart B

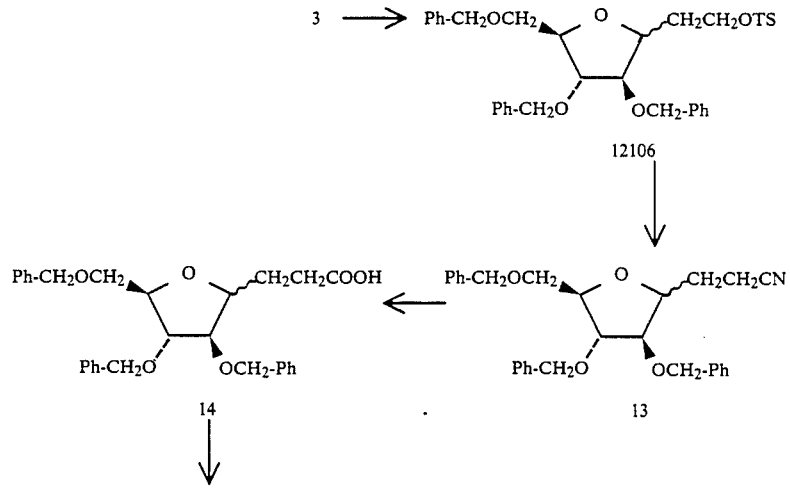

Flowchart B

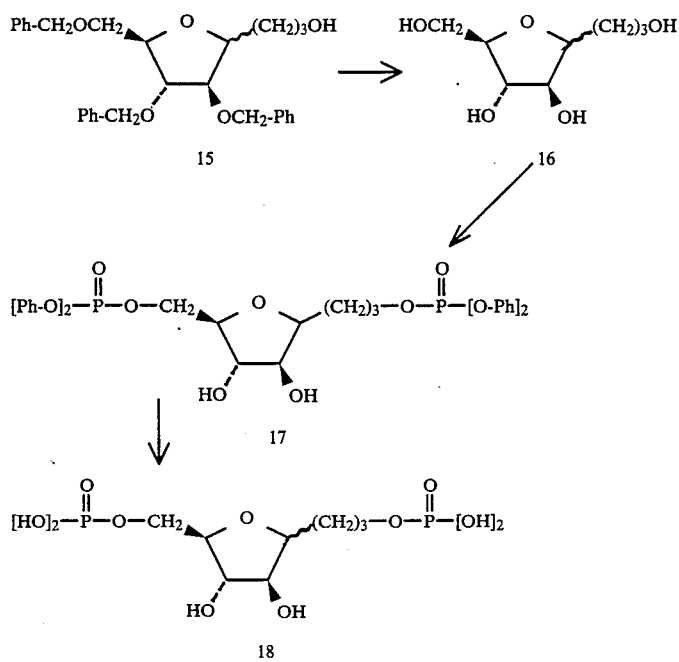

In accordance with Flowchart B, the mixture 3 (see Flowchart A) is treated with p-toluenesulfonyl chloride at reduced temperature, giving the mixture 12 which is treated with sodium cyanide in dimethyl sulfoxide at 85°–95° C., giving the mixture 4,7-anhydro-2,3-dideoxy-5,6,8-tris-O-(phenylmethyl)-D-gluco (and manno) octononitrile 13. The mixture 13 in ethanol is treated with potassium hydroxide and heat, giving the corresponding acid 14, which is treated with lithium aluminum hydride in ether at reflux, giving the mixture 4,7-anhydro-2,3-dideoxy-5,6,8-tris-O-(phenylmethyl)-D-qluco-octitol and 2,5-anhydro-6,7-dideoxy-1,3,4-tris-O-(phenylmethyl)-D-manno-octitol 15. Mixture 15 is then hydrogenated in methanol/glacial acetic acid over palladium on carbon, giving the mixture 4,7-anhydro-2,3-dideoxy-D-gluco (and manno)-octitol 16. The mixture 16 in pyridine is treated with diphenyl phosphorochloridate at reduced temperature, giving the mixture of products of Formula I where R′, R″, R‴ and R″″ are phenyl, 4,7-anhydro-2,3-dideoxy-D-gluco (and manno)-octitol, 1,8-bis (diphenyl phosphate) 17. Substitution of other esterifying agents, as described in Flowchart A, will result in corresponding tetraesters.

The mixture 17 may then be hydrogenated in methanol over platinum oxide, giving the mixture of products of Formula I where R′, R″, R‴ and R″″ are hydrogen, 4,7-anhydro-2,3-dideoxy-D-gluco (and manno)-octitol, 1,8-bis (dihydrogen phosphate) 18.

Flowchart C

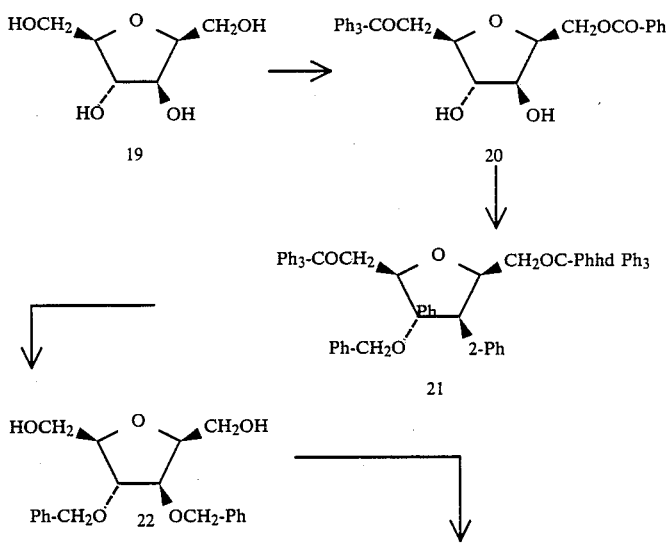

-continued

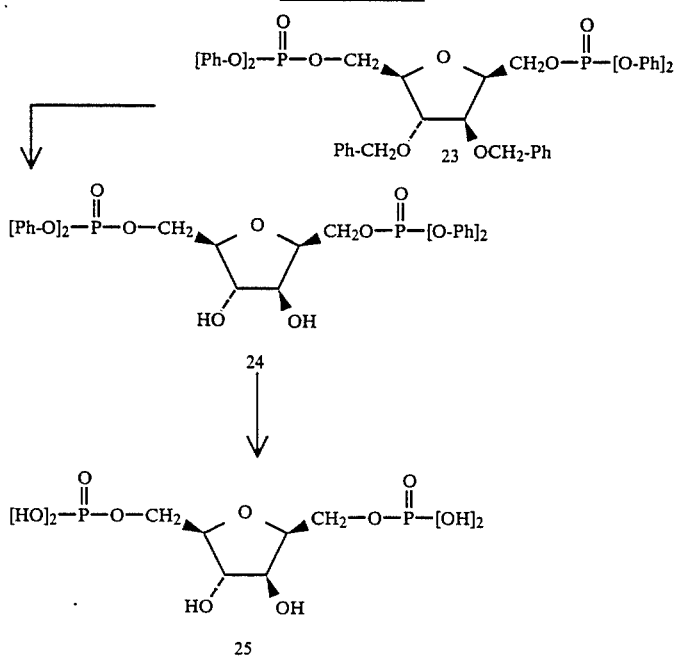

In accordance with Flowchart C, 2,5-anhydro-D-glucitol 19 is reacted with trityl chloride in pyridine, giving 2,5-anhydro-1,6-bis-O-(triphenylmethyl)-D-glucitol 20, which is then reacted with sodium hydride and benzyl bromide in dimethylformamide, giving 2,5-anhydro-3,4-bis-O-(phenylmethyl)-1,6-bis-O-(triphenylmethyl)-D-glucitol 21. Compound 21 is then reacted with acetic acid at about 80° C., giving 2,5-anhydro-3,4-bis-O-(phenylmethyl)-D-glucitol 22, which is then reacted with diphenyl phosphorochloridate in pyridine at reduced temperature, giving 2,5-anhydro-3,4-bis-O-(phenylmethyl)-D-glucitol, 1,6-bis(diphenyl phosphate) 23. Substitution of other esterifying agents as described in Flowchart A will result in the corresponding tetraesters. Compound 23 is then hydrogenated in methanol/acetic acid over palladium on carbon, giving the product of Formula I where R', R", R'" and R""are phenyl, 2,5-anhydro-D-glucitol, 1,6-bis(diphenyl phosphate) 24. which may then be hydrogenated in methanol over platinum oxide, giving the product of Formula I where R', R", R'" and R"" are hydrogen, 2,5-anhydro-D-glucitol, 1,6-bis(dihydrogen phosphate) 25. Compounds 24 and 25 are disclosed in Voll et al., *Carbohydrate Research*, 95, 145–154 (1981), but are prepared by a different process.

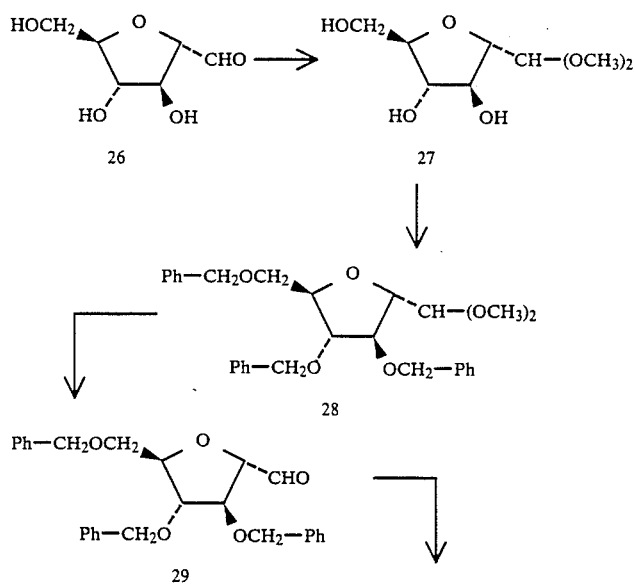

Flowchart D

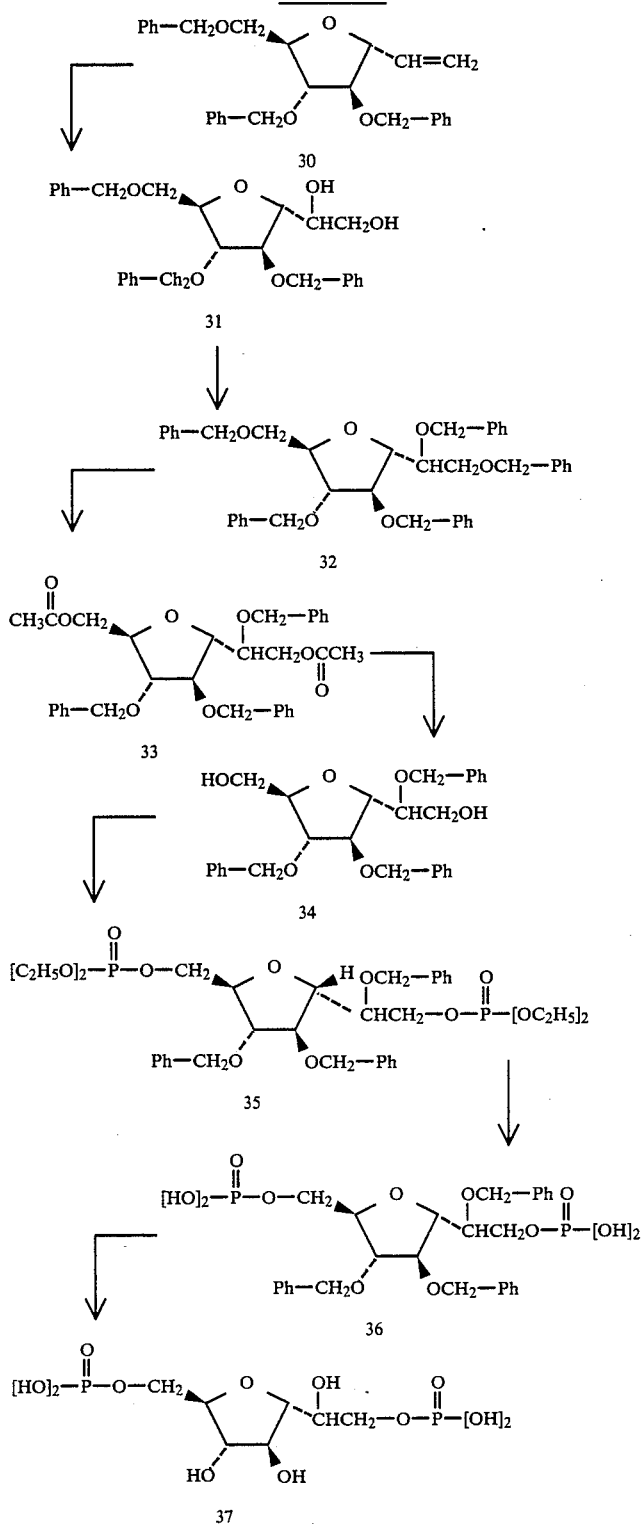

In accordance with Flowchart D, 2,5-anhydro-D-mannose 26 is treated with acetyl chloride in methanol at reflux, then neutralized with lead carbonate, giving 2,5-anhydro-D-mannose, dimethyl acetal 27. which is treated with sodium hydride and benzyl bromide in dimethylformamide, giving 2,5-anhydro-3,4,6-tris-O-(phenylmethyl)-D-mannose, dimethyl acetal 28. Compound 28 is then treated with tetrafluoroboric acid in acetonitrile, giving 2,5-anhydro-3,4,6-tris-O-(phenylmethyl)-D-mannose 29 which is then treated with Tebbe's reagent in ether at −40° C., then neutralized with sodium hydroxide, giving 3,6-anhydro-1,2-dideoxy-4,5,7- tris-O-(phenylmethyl)-D-manno-hept-1-enitol 30. Compound 30 is treated with osmium tetroxide in pyridine, giving 2,5-anhydro-1,3,4-tris-O-(phenylmethyl)-D-glycero-D-manno-heptitol 31, which is treated with sodium hydride in dimethylformamide, followed by treatment with benzyl bromide, giving 2,5-anhydro-1,3,4,6,7-pentakis-O-(phenylmethyl)-D-glycero-D-manno-heptitol 32. Compound 32 is treated with borontrifluoride etherate in acetic anhydride, giving 2,5-anhydro-3,4,6-tris-O-(phenylmethyl)D-glycero-D-manno-heptitol, 1,7-diacetate 33, which is treated with sodium ethoxide in ethanol, giving 2,5-anhydro-3,4,6-tris-O-(phenylmethyl)-D-glycero-D-manno-heptitol 34. Compound 34 is treated with diethyl phosphorochloridate in pyridine at reduced temperature, giving 2,5-anhydro-3,4,6-tris-O-(phenylmethyl)-D-glycero-D-manno-heptitol, 1,7-bis(diethyl phosphate) 35. Substituting other esterifying agents as described in Flowchart A will result in the corresponding tetraesters. Compound 35 is treated with bromotrimethyl silane in chloroform at reduced temperature, under an inert atmosphere, giving 2,5-anhydro-3,4,6-tris-O-(phenylmethyl)-D-glycero-D-manno-heptitol, 1,7-bis(dihydrogen phosphate) 36, which is then hydrogenated over palladium on carbon in methanol, giving the product of Formula I, where R', R", R'" and R"" are hydrogen, 2,5-anhydro-D-glycero-D-manno-heptitol, 1,7-bis(dihydrogen phosphate) 37.

mannitol, 1,6-bis(diphenyl phosphate) 40. Compound 40 is hydrogenated in methanol over platinum oxide, giving the product of Formula I where R', R",R'" and R"" are hydrogen, 2,5-anhydro-D-mannitol, 1,6-bis(dihydrogen phosphate) 41. Compounds 40 and 41 are disclosed in Voll et al., *Carbohydrate Research*, 95, 145–154 (1981), but are prepared by a different process. Substituting other phosphorylating agents in the reaction from 39 to 40, as described in Flowchart A, will result in the corresponding tetraesters and mixed tetraesters.

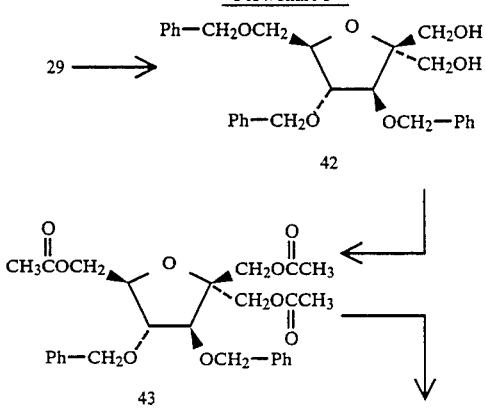

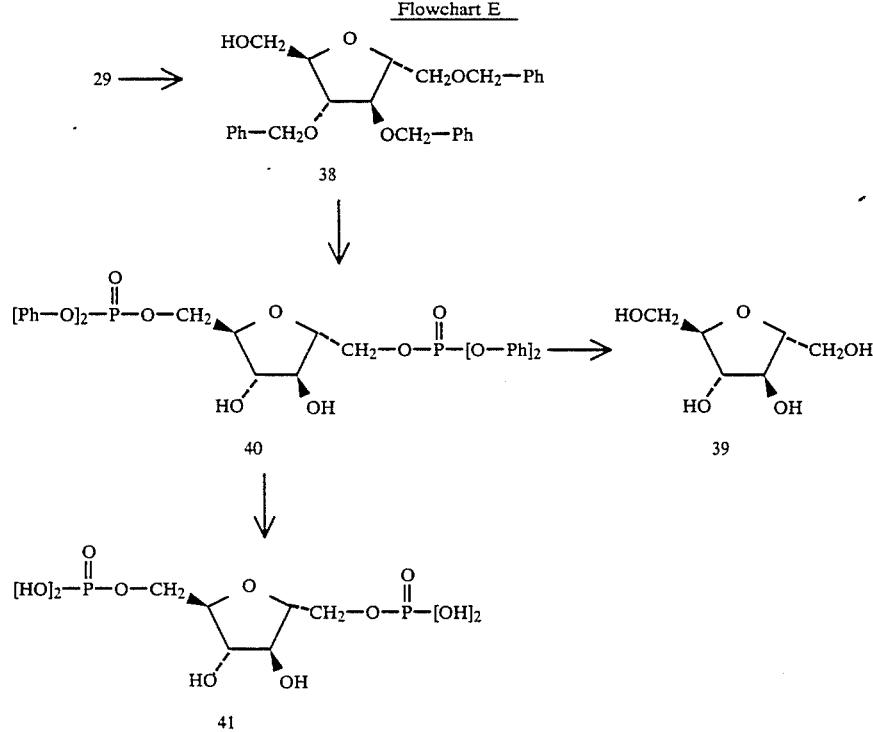

In accordance with Flowchart E, 2,5-anhydro-3,4,6-tris-O-(phenylmethyl)-D-mannose 29 is reacted with lithium aluminum hydride in ether at reflux temperature under argon, giving 2,5-anhydro-1,3,4-tris-O-(phenylmethyl)-D-mannitol 38. Compound 38 is hydrogenated in methanol/acetic acid over palladium on carbon, giving 2,5-anhydro-D-mannitol 39, which is then reacted with diphenyl phosphorochloridate in pyridine at reduced temperature, giving the product of Formula I where R', R",R'" and R"" are phenyl, 2,5-anhydro-D-

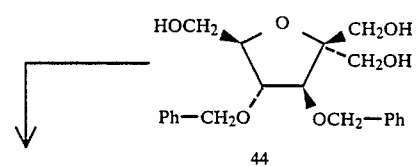

-continued
Flowchart F

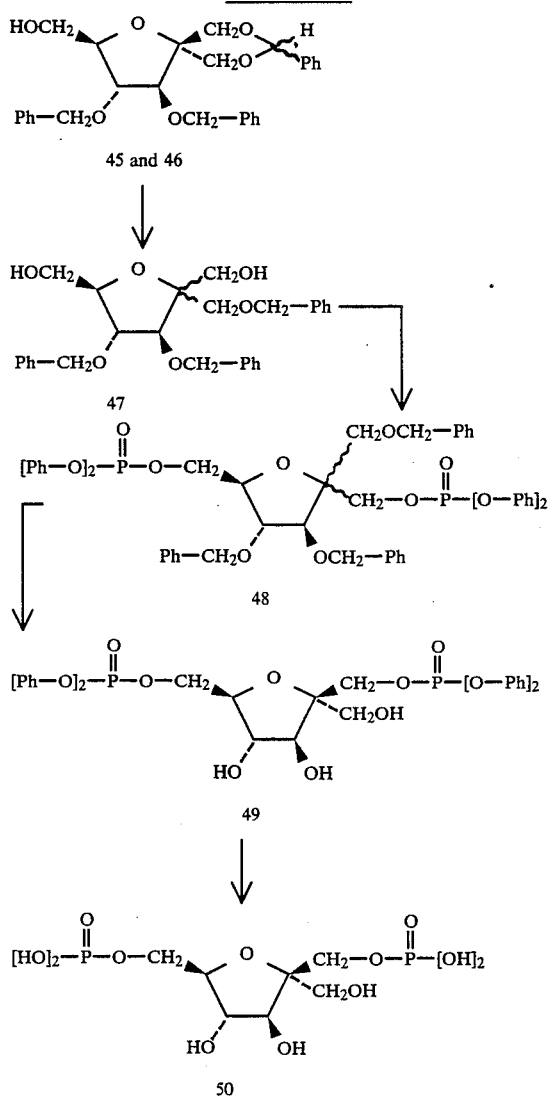

In accordance with Flowchart F, 2,5-anhydro-3,4,6-tris-O-(phenylmethyl)-D-mannose 29 is reacted with formalin and potassium carbonate in methanol at about 85° C. under an inert atmosphere, then acidified, giving 2,5-anhydro-2-C-(hydroxymethyl)-3,4,6-tris-O-(phenylmethyl)-D-glucitol 42. which is reacted with borontrifluoride etherate in acetic anhydride at reduced temperature followed by treatment with sodium bicarbonate, giving 2-C-[(acetyloxy)methyl]-2,5-anhydro-3,4-bis-O-(phenylmethyl)-D-glucitol, 1,6-diacetate 43. Compound 43 is reacted with aqueous potassium carbonate in methanol at reflux, giving 2,5-anhydro-2-C-(hydroxymethyl)-3,4-bis-O-(phenylmethyl)-D-glucitol 44, which is reacted with benzaldehyde dimethyl acetal and p-toluenesulfonic acid in dimethylformamide at about 60° C. under reduced pressure, giving a mixture of [R] and [S]-2,5-anhydro-2-C-(hydroxymethyl)-3,4-bis-O-(phenylmethyl)-1,2$^1$-O-(phenylmethylene)-D-glucitol 45 and 46. The mixture 45 and 46 is reacted with aluminum chloride and lithium aluminum hydride in ether/dichloromethane under an inert atmosphere, giving a mixture of 2,5-anhydro-2-C-[(phenylmethoxy)methyl]-3,4-bis-O-(phenylmethyl)-D-glucitol and 2,5-anhydro-2-C-(hydroxymethyl)-1,3,4-tris-O-(phenylmethyl)-D-glucitol 47, which is reacted with diphenyl phosphorochloridate in pyridine at reduced temperature, giving a mixture of 2,5-anhydro-2-C-[(phenylmethoxy)methyl]-3,4-bis-O-(phenylmethyl)-D-glucitol, 1,6-bis (diphenyl phosphate) and 2,5-anhydro-2-C-[[(diphenoxyphosphinyl)oxy]methyl]-1, 3,4-tris-O-(phenylmethyl)-D-glucitol, 6-diphenyl phosphate 48. The mixture 48 is hydrogenated in methanol and acetic acid over palladium on carbon, giving, after chromatography, the product of Formula I where R′, R″, R‴ and R″″ are phenyl, 2,5-anhydro-2-C-(hydroxymethyl)-D-glucitol, 1,6-bis(diphenyl phosphate) 49. Substitution of other esterifying agents as described in Flowchart A will result in the corresponding tetraesters. Compound 49 may then be hydrogenated in methanol over platinum oxide, giving the product of Formula I where R′, R″, R‴ and R″″ are hydrogen, 2,5-anhydro-2-C-(hydroxymethyl)-D-glucitol, 1,6-bis(dihydrogen phosphate) 50.

Flowchart G

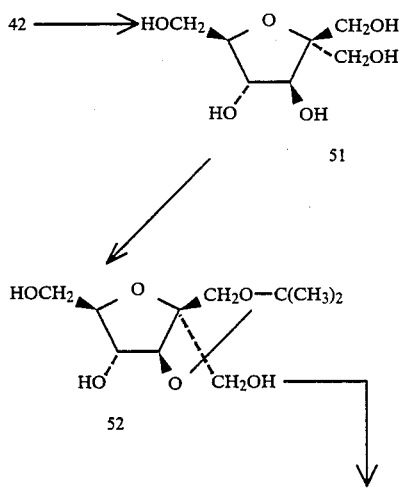

Flowchart G

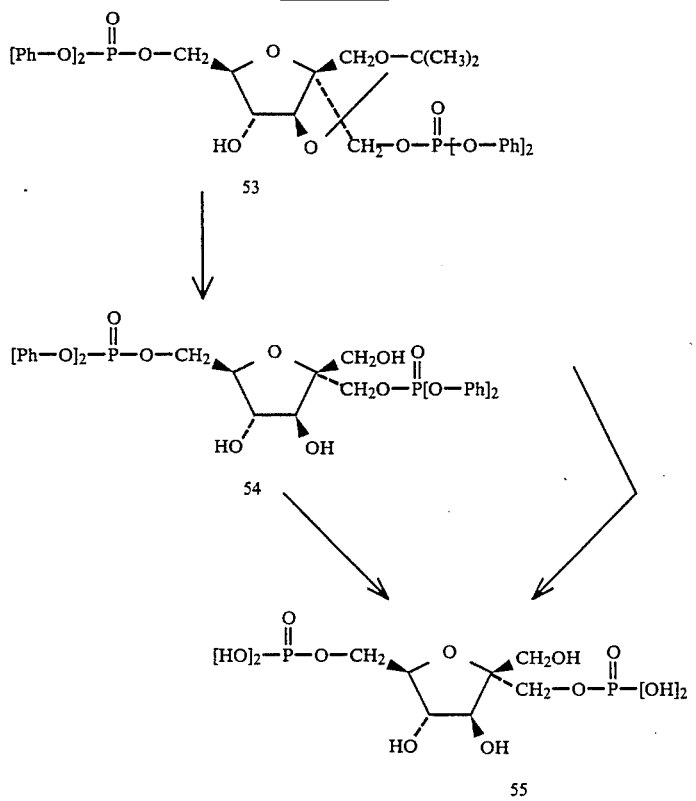

In accordance with Flowchart G, 2,5-anhydro-2-C-(hydroxymethyl)-3,4,6-tris-O-(phenylmethyl)-D-glucitol 42 is hydrogenated in methanol/acetic acid over palladium on carbon, giving 2,5-anhydro-2-C-(hydroxymethyl)-D-glucitol 51, which is treated with copper sulfate and sulfuric acid in acetone, then neutralized, giving 2,5-anhydro-2-C-(hydroxymethyl)-2$^1$,3-O-(1-methylethylidene)-D-glucitol 52. Compound 52 is reacted with diphenyl phosphorochloridate in pyridine at reduced temperature, giving 2,5-anhydro-2-C-[[(diphenoxyphosphinyl)oxy]methyl]-1,3-O-(1-methylethylidene)-D-glucitol, 6-(diphenyl phosphate) 53, which is then treated with 80% aqueous acetic acid at 80° C., giving 2,5-anhydro-2-C-[[(diphenoxyphosphinyl)oxy]methyl]-D-glucitol, 6-(diphenyl phosphate) 54. Substitution of other esterifying agents as described in Flowchart A will result in the corresponding tetraesters. Compound 53 is hydrogenated in methanol over platinum oxide, giving directly the product 2,5-anhydro-2-C-[(phosphonooxy)methyl]-D-glucitol, 6-(dihydrogen phosphate) 55. Compound 54 may be hydrogenated under the same conditions, giving 55.

Flowchart H

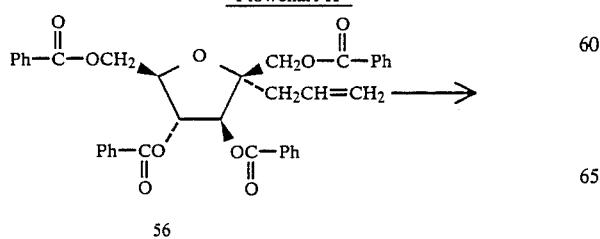

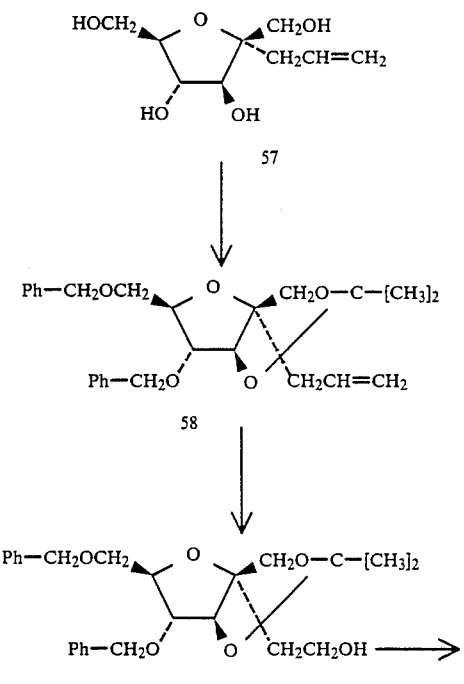

-continued
Flowchart H

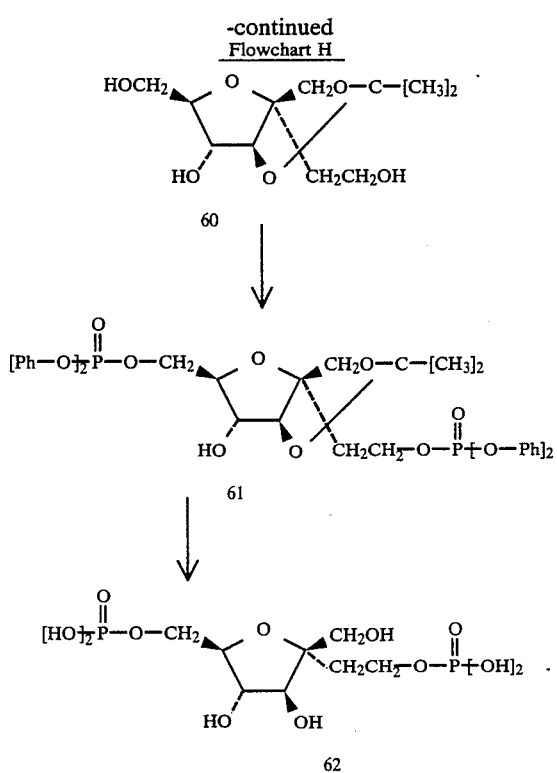

In accordance with Flowchart H, D-fructofuranose, pentabenzoate and allyltrimethylsilane are reacted in acetonitrile at reduced temperature, in the presence of borontrifluoride etherate, giving 4,7-anhydro-4-C-[(benzoyloxy)methyl]-1,2,3-trideoxy-D-arabino-oct-1-enitol, 5,6,8-tribenzoate 56, which is reacted with sodium methoxide in methanol, giving 4,7-anhydro-1,2,3-trideoxy-4-C-(hydroxymethyl)-D-manno-oct-1-enitol 57. Compound 57 is reacted with copper sulfate and sulfuric acid in acetone, then neutralized giving $4^1,1,5:4,7$-dianhydro-1,2,3-trideoxy-4-C-[(1-hydroxy-1-methylethoxy)methyl]-6,8-bis-O-(phenylmethyl)-D-manno-oct-1-enitol 58, which is first subjected to ozonolysis in a mixture of pyridine and dichloromethane and then reduced with sodium borohydride in ethanol, giving $3,6:3^1,4$-dianhydro-2-deoxy-3-C-[(1-hydroxy-1-methylethoxy)methyl]-5,7-bis-O-(phenylmethyl)-D-manno-heptitol 59. Compound 59 is hydrogenated in methanol/acetic acid over palladium on carbon, giving $3,6:3^1,4$-dianhydro-2-deoxy-3-C-[(1-hydroxy-1-methylethoxy)methyl]-D-manno-heptitol 60, which is reacted with diphenyl phosphorochloridate in pyridine at reduced temperature, giving the product $3,6:3^1,4$-dianhydro-2-deoxy-3-C-[(1-hydroxy-1-methylethoxy)-methyl]-D-manno-heptitol, 1.7-bis-(diphenyl phosphate) 61, which is hydrogenated in methanol over platinum oxide, giving the product 3,6-anhydro-2-deoxy-3-C-(hydroxymethyl)-D-manno-heptitol, 1,7-bis(dihydrogen phosphate) 62.

Flowchart I

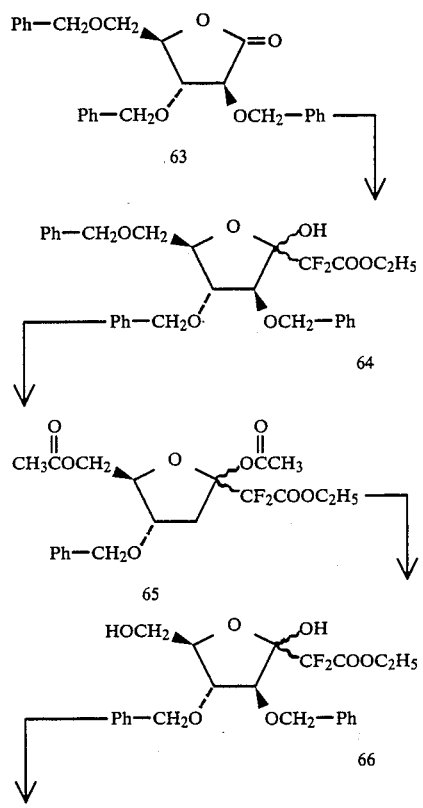

Flowchart I

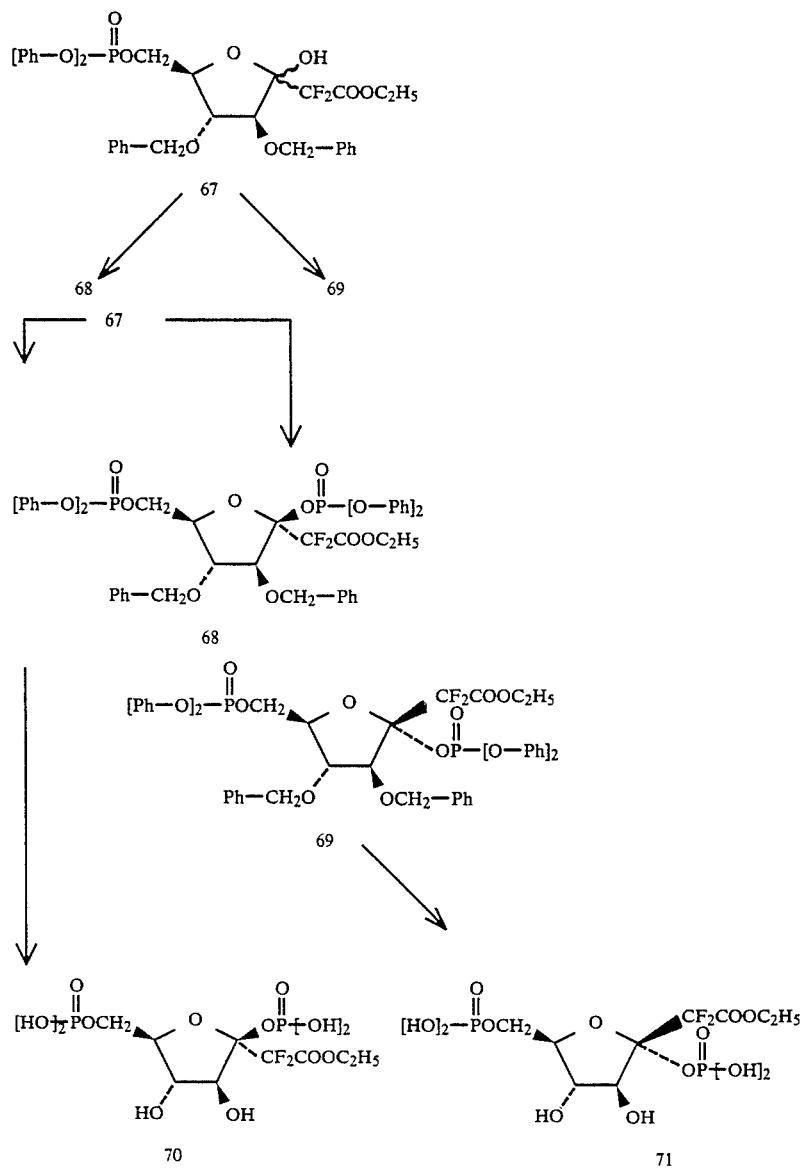

In accordance with Flowchart I, treatment of 2,3,5-tris-O-(phenylmethyl)-D-arabinonic acid-gamma-lactone 63 with zinc dust in tetrahydrofuran and ethyl bromodifluoroacetate provides the furanose ester 64. Compound 64 is treated with boron trifluoride etherate in acetic anhydride to effect selective debenzylation of the primary benzyl ether and provide the diacetate 65. Compound 65 is deacetylated with ethanolic sodium ethoxide to provide the diol 66. Diol 66 is phosphorylated with diphenyl phosphorochloridate in pyridine providing the monophosphate triester 67. Further phosphorylation of 67 with diphenyl phosphorochloridate with catalysis by dimethylaminopyridine provides the separable mixture of the β and α forms of the bis(diphenyl phosphate) 68 and 69. respectively. Successive hydrogenolysis of the benzyl protecting groups in the presence of palladium on carbon and the phenyl protecting groups in the presence of platinum provides the β and α forms of the bis(dihydrogen phosphate) 70 and 71respectively, isolated as the sodium salt.

Flowchart J

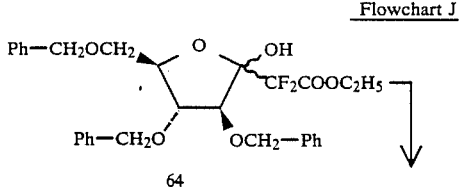

Flowchart J
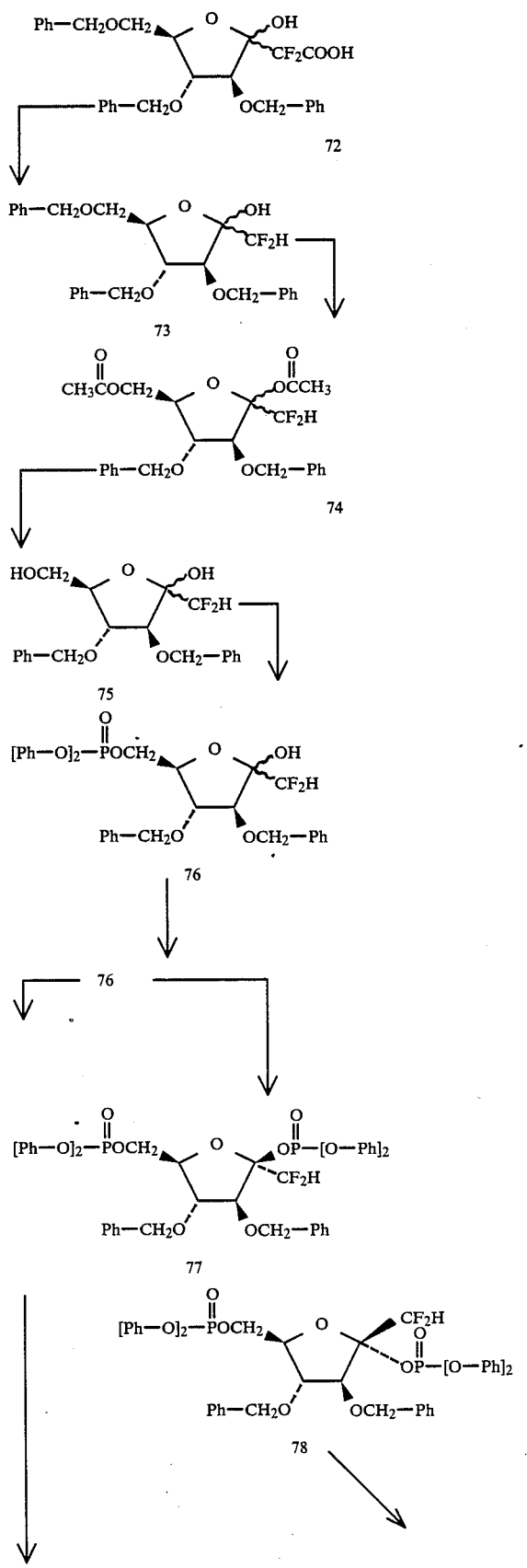

Flowchart J -continued

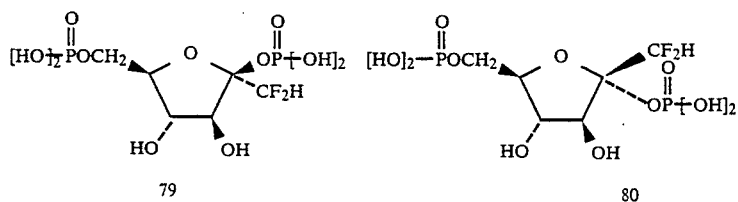

In accordance with Flowchart J, the ester 64 is saponified with sodium hydroxide, giving the acid 72. Decarboxylation of 72 to the -1-deoxy-1,1-difluorofructose derivative 73 is effected in boiling 2,6-lutidine. Compound 73 is treated with boron trifluoride etherate in acetic anhydride to effect selective debenzylation of the primary benzyl ether and provide the diacetate 74. Compound 74 is deacetylated with sodium methoxide in methanol, giving diol 75. Diol 75 is phosphorylated with diphenyl phosphorochloridate in pyridine to provide the monophosphate triester 76. Further phosphorylation of 76 with diphenyl phosphorochloridate with catalysis by dimethylaminopyridine provides a separable mixture of the β and α forms of the bis(diphenyl phosphates) 77 and 78, respectively. Successive hydrogenolysis of the benzyl protecting groups in the presence of palladium on carbon and the phenyl protecting groups in the presence of platinum provides the β and α forms of the bis(dihydrogen phosphates) 79 and 80 respectively, isolated as the disodium salts.

In a modification of this procedure, the diol 75 is converted to the bis(dibenzyl phosphate) counter-parts of the bis(diphenyl phosphate) compounds 77 and 78 of Flowchart J by treating the diol 75 at −78° C. with n-butyllithium to provide a tetrahydrofuran solution of the dianion, which is reacted with tetrabenzyl pyrophosphate to provide a separable mixture of the β and α forms of the bis(dibenzyl phosphate) compounds. Hydrogenolysis of the benzyl protecting groups in the presence of palladium hydroxide, followed by neutralization with sodium bicarbonate provides the β and α forms of the bis(dihydrogen phosphates), isolated as the tetrasodium salts.

In a further embodiment of this procedure, the monofluoro analogue to the difluoro acid 72 is reacted in accordance with Flowchart J, producing the monophosphate triester analogue to 76. Hydrogenolysis of the benzyl protecting groups in the presence of palladium hydroxide, followed by neutralization with sodium bicarbonate provides the monofluoro bis(dihydrogen phosphates), isolated as the disodium salts.

Flowchart K

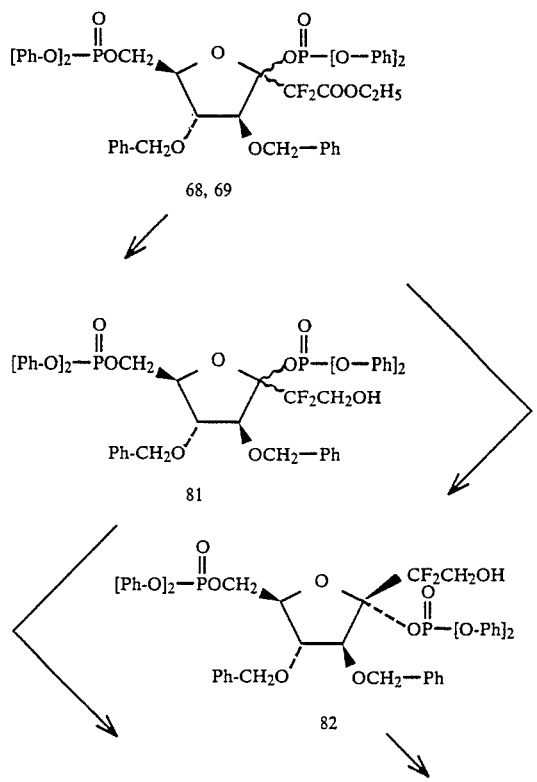

Flowchart K

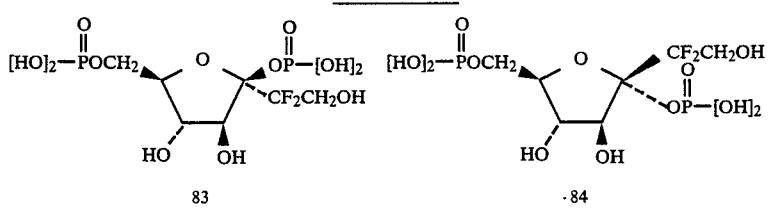

In accordance with Flowchart K, treatment of D-arabino-3-heptulofuranosonic acid, 2-deoxy-2,2-difluoro-4,5-bis-O-(phenylmethyl)ethyl ester, bis(diphenyl phosphate) 68 and 69 with sodium borohydride in ethanol affords a separable mixture of the β and α forms of the 2-deoxy-2,2-difluoroheptulofuranose 81 and 82, respectively. Successive hydrogenolysis of the benzyl protecting groups in the presence of palladium on carbon and the phenyl protecting groups in the presence of platinum, provides the β and α forms of the 3,7-bis(-dihydrogen phosphates) 83 and 84, respectively, isolated as the disodium salts.

Flowchart L

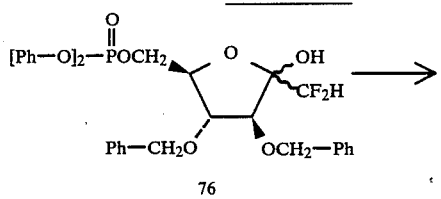

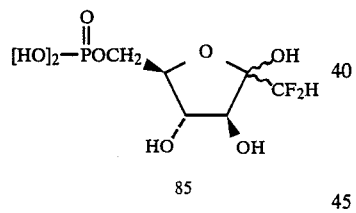

In accordance with Flowchart L, the monophosphate triester 76 is deprotected by successive hydrogenolysis of the benzyl protecting groups in the presence of palladium hydroxide and the phenyl protecting groups in the presence of platinum to provide the dihydrogen phosphate 85, isolated as the sodium salt.

In a modification of the above procedure, the —CF$_2$H group of the monophosphate triester is replaced by CH$_2$F, so that the two-stage hydrogenolysis provides the corresponding dihydrogen phosphate. The —CF$_2$H group may also be replaced by CF$_3$ or CF$_2$CH$_2$OH, so that the two-stage hydrogenolysis would provide the corresponding dihydrogen phosphate.

Flowchart M

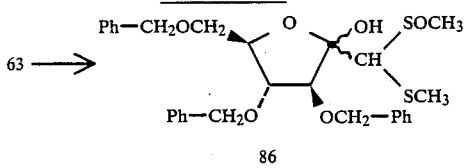

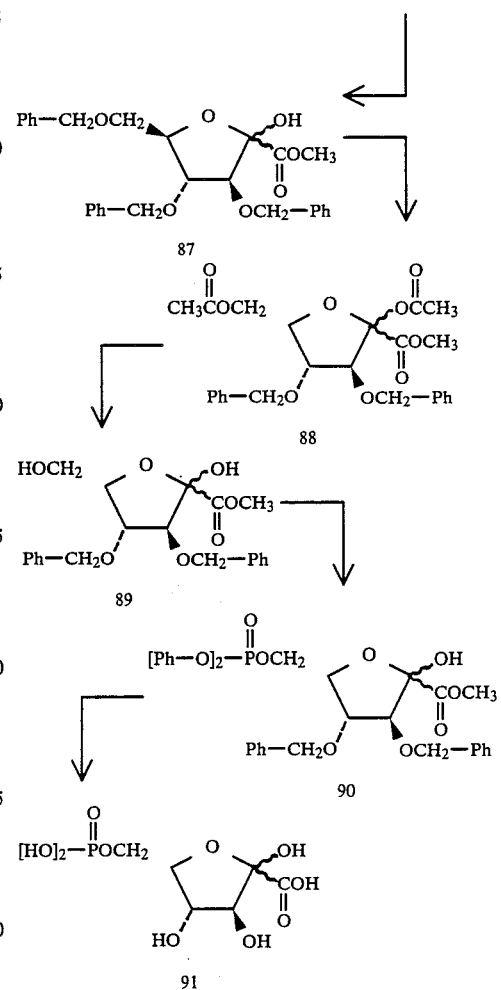

In accordance with Flowchart M, treatment of 2,3,5-tris-O-(phenylmethyl)-D-arabinonic acid-gamma-lactone 63 with lithio methyl (methylthiomethyl) sulfoxide in tetrahydrofuran provides the adduct 86. Reaction of 86 with cupric chloride-cupric oxide in methanol provides the methyl hexulosonate 87. Compound 87 is treated with boron trifluoride etherate in acetic anhydride to effect selective debenzylation of the primary benzyl group and provide the diacetate 88. Deacetylation of 88 with methanolic sodium methoxide provides the diol 89. Diol 89 is phosphorylated with diphenyl phosphorochloridate in pyridine to provide the monophosphate triester 90. Successive hydrogenolysis of the benzyl groups in 90 by palladium hydroxide in methanol and the phenyl groups by platinum in methanol provides the dihydrogen phosphate carboxylic acid 91, isolated as the sodium salt.

In a modification of the above procedure, the ethyl ester 64 is subjected to hydrogenolysis and neutralization with sodium bicarbonate to provide the corresponding dihydrogen phosphate carboxylic acid, isolated as the sodium salt.

Certain of the phosphate esters of Formula I may be prepared according to the following scheme:

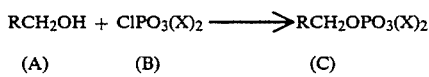

$$RCH_2OH + ClPO_3(X)_2 \longrightarrow RCH_2OPO_3(X)_2$$

(A)         (B)                    (C)

An alcohol (A), which refers to structures I-VIII in Table I, is reacted with a chlorophosphate (B), where X refers independently to any of groups a-t (R', R", R''' or R'''' from Formula I) in Table I, in pyridine at ice bath temperature, giving the bisphosphate esters (C) which refer to structures IX-XVII in Table I.

As an example of the above procedure, a one mmol solution of 2,5-anhydro-D-mannitol (compound I, Table I, Example 30) in 2 ml of anhydrous pyridine was cooled in an ice bath and treated with 2.2 mmol of diethyl chlorophosphate [ClPO$_3$(X)$_2$ (where X is j, Table I)] under argon. The mixture was stirred at 0°-5° C. for 4 hours and then warmed to room temperature. After 30 minutes, 100 μl of water was added and stirring was continued for an additional 30 minutes. The volatiles were removed in vacuo and the residue taken up in dichloromethane/water. The organic layer was washed sequentially with cold 1N hydrochloric acid, water, saturated sodium bicarbonate, water and brine, then dried. Removal of the solvent gave 275 mg of a yellow oil. Flash chromatography on silica gel, eluting with 4% methanol in dichloromethane gave a colorless oil (Rf=0.14) which was characterized as compound IX j (see Table I) by $^{13}$C NMR and $^1$HNMR analyses.

Following the above procedure, the reaction of I with ClPO$_3$(X)$_2$ where X is a produced IX a, [2,5-anhydro-D-mannitol, 1,6-bis(diphenyl phosphate), the product of Example 31]; reaction of VI with X=a produced XIV a, [4,7-anhydro-2,3-dideoxy-D-gluco (and manno)-octitol, 1,8-bis (diphenyl phosphate), the product of Example 11]; and the reaction of VIII with X=a produced XVII a, [3,6:3$^1$,4-dianhydro-2-deoxy-3-C-[(1-hydroxy-1-methylethoxy)methyl]-D-manno-heptitol, 1,7-bis(diphenyl phosphate), the product of Example 50], after deprotection of the acetonide with aqueous acetic acid, or with iodine in refluxing methanol, followed by the phosphorylation step.

In an example of a variation of the above procedure, a dry 360 mg sample of 3,6-anhydro-2-deoxy-4,5-bis-O-(phenylmethyl)-D-manno-heptitol (Compound III, Table I, Example 52) in 1.7 ml of pyridine was treated at ice bath temperature under argon with 4 mmol of diethyl chlorophosphate. The mixture was stirred at 0°-5° C. for 4 hours and then warmed to room temperature. After 30 minutes, 100 μl of water was added and stirring continued for an additional 30 minutes. The volatiles were removed in vacuo and the residue taken up in dichloromethane/water. The organic layer was washed sequentially with cold 1N hydrochloric acid, water, saturated sodium bicarbonate, water and brine, then dried and the solvent removed. Chromatography on silica gel, eluting with 1% methanol in dichloromethane followed by 2.5% methanol in dichloromethane gave an oil. This oil was dissolved in 20 ml of methanol and hydrogenated at 70 psi over 20% palladium hydroxide on carbon. After 6 hours, the completed reaction mixture was filtered and the solvent removed. The residue was chromatographed on silica gel, eluting with 3% methanol in dichloromethane (Rf=0.1) and then with 5% methanol in dichloromethane (Rf=0.3) giving a 60% overall yield of a colorless oil which was characterized as compound XI j by $^{13}$C NMR and $^1$H NMR analysis.

Following the above procedure, the reaction of II with X is a produced X a [2,5-anhydro-D-glucitol, 1,6-bis (diphenyl phosphate), the product of Example 18]; reaction of III with X is a produced XI a; reaction of IV with X is a produced XII a; reaction of V with X is a produced XIII a; reaction of V with X is j produced XIII j; reaction of VII with X is a produced XV a [2,5-anhydro-2-C-(hydroxymethyl)-D-glucitol, 1,6-bis (diphenyl phosphate), the product of Example 39] as well as XVI a, the D-mannitol isomer, which were separated by chromatography.

TABLE I (Ph = phenyl)

| Alcohols | Bisphosphate | ClPO$_3$(X)$_2$ X = |
|---|---|---|
| I (HOCH$_2$—furanose ring with HO, OH, CH$_2$OH) | IX (R'''O, R''''O-P(O)-O-CH$_2$—furanose—CH$_2$-O-P(O)(OR')(OR'')) | a (phenyl) |
| II (HOCH$_2$—furanose ring with Ph-CH$_2$O, OCH$_2$-Ph, CH$_2$OH) | X (R'''O, R''''O-P(O)-O-CH$_2$—furanose—CH$_2$-O-P(O)(OR')(OR'')) | b (4-methylphenyl) |

TABLE I-continued
(Ph = phenyl)

| Alcohols | Bisphosphate | ClPO$_3$(X)$_2$ X = |
|---|---|---|
| III | XI | c: $-C(CH_3)_3$ substituted phenyl (o-tert-butyl) |
| IV | XII | d: 2,4,6-trimethylphenyl |
| V | XIII | e: y-substituted phenyl; y = alkyl, alkoxy, NO$_2$, halogen |
| | | f: o-chlorophenyl |
| | | g: benzyl (PhCH$_2$—) |
| VI | XIV | h: y-substituted benzyl; y = alkyl, alkoxy, NO$_2$, halogen |
| VII | XV | i: CH$_3$— <br> j: C$_2$H$_5$— |
| | XVI | k: n-alkyl(C$_3$–C$_{18}$), iso-alkyl(C$_3$–C$_8$), cycloalkyl(C$_3$–C$_6$) <br> l: Cl$_3$CCH$_2$— |
| | | m: CH$_2$=CHCH$_2$— <br> ZCH$_2$CH$_2$ <br> X = SO$_2$R$_2$, SR$_2$, Si(R$_2$)$_3$ <br> R$_2$ = alkyl (C$_1$–C$_3$) |

TABLE I-continued
(Ph = phenyl)

| Alcohols | Bisphosphate | ClPO$_3$(X)$_2$ X = |
|---|---|---|
| 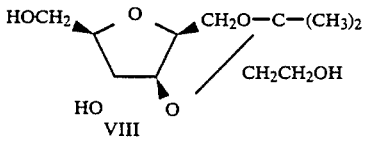 VIII | 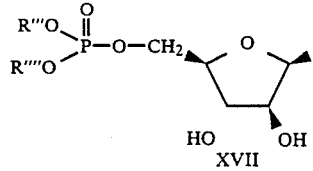 XVII | 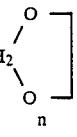 halo, CH$_2$ n |
| | |  R$_3$ = alkyl, R$_3$-R$_3$ = alkylene, acetal o |
| | | 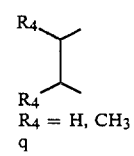 p |
| | | 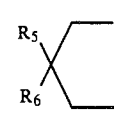 R$_4$ = H, CH$_3$ q |
| | | 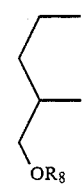 R$_5$ = R$_6$ = H, F, C$_1$-C$_4$ alkyl; R$_5$ = H; R$_6$ = F, OH, OR$_7$ R$_7$ = alkyl (C$_1$-C$_6$), cycloalkyl, aryl r |
| | | 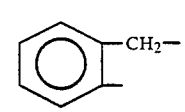 R$_8$ = H, alkyl (C$_1$-C$_{18}$), aryl s |
| | | [benzyl structure] t H u |

Other examples of phosphate esters which can be prepared by the above methods are shown in Table II, wherein the references to structures are identified as in Table I.

TABLE II
| Alcohol | ClPO₃(X)*₂ X = | Further Deprotection | Product |
|---|---|---|---|
| I | 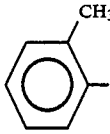 (2-methylphenyl) | None | IX b |
| | 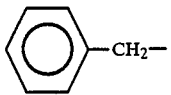 (benzyl, C₆H₅CH₂—) | None | IX g |
| | CH₃— | None | IX i |
| | C₈H₁₇— | None | IX k |
| | Cl₃CCH₂— | None | IX l |
| | 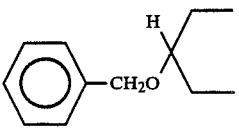 | None | IX r |
| | 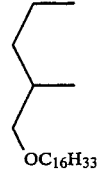 | None | IX s |
| II | 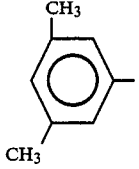 (2,4-dimethylphenyl) | H₂/Pd(OH)₂ | X d |
| | 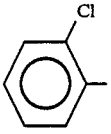 (2-chlorophenyl) | H₂/Pd(OH)₂** | X f |
| | 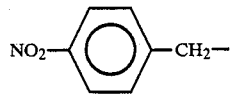 (4-nitrobenzyl) | H₂/Pd(OH)₂** | X h |
| | C₂H₅— | H₂/Pd(OH)₂ | X j |
| | isopropyl | H₂/Pd(OH)₂ | X k |
| | 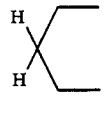 | H₂/Pd(OH)₂ | X r |
| | 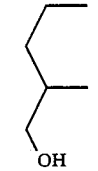 | H₂Pd(OH)₂ | X s |

TABLE II-continued

| Alcohol | ClPO₃ (X)*₂ X = | Further Deprotection | Product |
|---|---|---|---|
| III | 2-methylphenyl | H₂/Pd(OH)₂ | XI b |
| | 4-methoxyphenyl | H₂/Pd(OH)₂ | XI e |
| | 2-chlorophenyl | H₂/Pd(OH)₂ | XI f |
| | benzyl (PhCH₂–) | H₂/Pd(OH)₂** | XI g |
| | C₁₇H₃₅– | H₂/Pd(OH)₂ | XI k |
| | CH₃OCH₂CH₂– | H₂/Pd(OH)₂ | XI n |
| | CH(CH₃)(CH₂–)(CH₂OCH₃) [CH₃O-CH with ethyl groups] | H₂/Pd(OH)₂ | XI r |
| | 2-methyl-3-methoxypropyl | H₂/Pd(OH)₂ | XI s |
| | benzyl (PhCH₂–) | H₂/Pd(OH)₂** | XI t |
| IV | 2-(tert-butyl)phenyl, CH(CH₃)₃ | H₂/Pd(OH)₂ | XII c |
| | 4-methoxyphenyl | H₂/Pd(OH)₂ | XII e |
| | 2-chlorophenyl | H₂/Pd(OH)₂ | XII f |
| | 4-methoxybenzyl (CH₃O-C₆H₄-CH₂–) | H₂/Pd(OH)₂** | XII h |
| | CH₃– | H₂/Pd(OH)₂ | XII i |
| | isobutyl- | H₂/Pd(OH)₂ | XII k |

TABLE II-continued

| Alcohol | ClPO₃(X)*₂ X = | Further Deprotection | Product |
|---|---|---|---|
| | CH₂=CHCH₂— | H₂/Pd(OH)₂** | XII m |
| | CH₃SCH₂CH₂— | H₂/Pd(OH)₂ | XII n |
| | 2-ethyl-hexyl-OC₄H₁₀ group | H₂/Pd(OH)₂ | XII s |
| V | 4-methylphenyl (CH₃—C₆H₄—) | H₂/Pd(OH)₂ | XIII b |
| | CH₃— | H₂/Pd(OH)₂ | XIII i |
| | n-C₄H₉ | H₂/Pd(OH)₂ | III k |
| | isopropyl (H–C(H)(Et)Et) | H₂/Pd(OH)₂ | XIII r |
| | 2-ethyl-hexyl-OC₁₈H₃₇ group | H₂/Pd(OH)₂ | XIII s |
| VI | Cl—C₆H₄— | None | XIV e |
| | C₆H₅—CH₂— (benzyl) | None | XIV g |
| | C₂H₅— | None | XIV j |
| | cyclohexyl | None | XIV k |
| | Cl₃CCH₂ | None | XIV l |
| | CF₂ group (F₂C(Et)Et) | None | XIV r |
| VII | 3,5-dimethylphenyl (CH₃, CH₃ on ring) | H₂/Pd(OH)₂ | XV d & XVI d*** |
| | isopropyl—C₆H₄— | H₂/Pd(OH)₂ | XV e & XVI e*** |

TABLE II-continued

| Alcohol | ClPO$_3$(X)*$_2$<br>X = | Further Deprotection | Product |
|---|---|---|---|
| | CH$_3$— | H$_2$/Pd(OH)$_2$ | XV i & XVI i*** |
| | C$_2$H$_5$— | H$_2$/Pd(OH)$_2$ | XV j & XVI j*** |
| VII | C$_8$H$_{17}$— | H$_2$/Pd(OH)$_2$ | XV k & XVI k*** |
| | 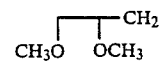 | H$_2$Pd(OH)$_2$ | XV o & XVI o*** |
| |  | H$_2$/Pd(OH)$_2$ | XV r & XVI r*** |
| VIII | 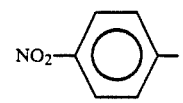 | aqueous acetic acid, or I$_2$/CH$_3$OH | XVII e |
| | 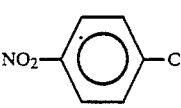 | aqueous acetic acid, or I$_2$/CH$_3$OH | XVII h |
| | CH$_3$— | aqueous acetic acid, or I$_2$/CH$_3$OH | XVII i |
| | C$_2$H$_5$— | aqueous acetic acid, or I$_2$/CH$_3$OH | XVII j |
| | CH$_2$=CHCH$_2$— | aqueous acetic acid, or I$_2$/CH$_3$OH | XVII m |
| | C$_2$H$_5$SO$_2$CH$_2$CH$_2$— | aqueous acetic acid, or I$_2$/CH$_3$OH | XVII n |
| | 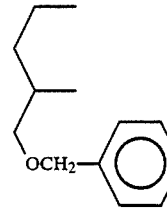 | aqueous acetic acid, or I$_2$/CH$_3$OH | XVII s |

*Reagents are commercially available or are synthesized according to L. A. Slotin, Synthesis, 737 (1977); K. Sasse in Houben-Weyl, Methoden der Organischen Chemie, 4th Edition, Vol. XII/2, E. Miller Ed., Georg Thieme Verlag, Stuttgart (1964); R. N. Hunston, et al. J. Med. Chem., 27, 440 (1984); P. Halvary and J. Weller, Helv. Chim. Acta., 69, 1862 (1968). Reagents for mixed esters (R' not equal to R" or R'" not equal to R"") are synthesized using the same methods.
**Requires hydrogenation before phosphorylation.
***XV and XVI are separable by chromatography.

Certain of the phosphate esters of Formula I may be prepared according to the following scheme.

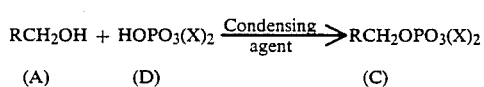

An alcohol (A), which refers to structures I–VIII in Table I, is reacted with a phosphate (D), where X refers independently to any of groups a–t (R', R", R'" and R"" from Formula I) in Table I, and a condensing agent such as triphenylphosphine and diethylazodicarboxylate in toluene at ice bath temperature. After stirring at 70° C., the mixture is recooled to 5° C., filtered and the filtrate evaporated. The residue is chromatographed as described above, then debenzylated and purified, giving the bisphosphate esters (C) which refer to structures IX–XVII in Table I.

As an example of the above procedure, a 2 mmol portion of diethylazodicarboxylate is added dropwise, with stirring to a cold (0°–5° C.) solution of 2 mmol of diethyl phosphate (HPO$_3$(X)$_2$ where X is j in Table I), 2 mmol of triethylphosphine and 1 mmol of 3.,6-anhydro-2-deoxy-4,5-bis-O-(phenylmethyl)-D-manno-heptitol (III, Table I, Ex. 52) in toluene. The resulting mixture is stirred at 70° C. for 5 hours, then cooled to 5+ C. and filtered. The filtrate is evaporated and the residue chromatographed, debenzylated and purified as described above, giving product XI j.

Other examples of phosphate esters which can be prepared by the above method are shown in Table III, wherein the references to structures are identified as in Table I.

TABLE III

| Alcohol | HOPO$_3$(X)$_2$*<br>X = | Further Deprotection | Product |
|---|---|---|---|
| I |  | None | IX a |

TABLE III-continued

| Alcohol | HOPO$_3$(X)$_2$* X = | Further Deprotection | Product |
|---|---|---|---|
| | 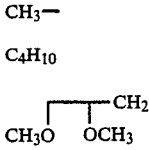—CH$_2$— | None | IX g |
| | CH$_3$— | None | IX i |
| | C$_4$H$_{10}$ | None | IX k |
| | CH$_3$O——OCH$_3$ (with CH$_2$—) | None | IX o |
| II |  | H$_2$/Pd(OH)$_2$ | X a |
| | C$_2$H$_5$— | H$_2$/Pd(OH)$_2$ | X j |
| |  (H,H) | H$_2$/Pd(OH)$_2$ | X r |
| III | 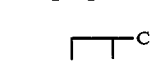 | H$_2$/Pd(OH)$_2$ | XI a |
| | CH$_3$— | H$_2$/Pd(OH)$_2$ | XI i |
| | ClCH$_2$CH$_2$— | H$_2$/Pd(OH)$_2$ | XI n |
| | C$_{16}$H$_{33}$O——OC$_{16}$H$_{33}$ (with CH$_2$—) | H$_2$/Pd(OH)$_2$ | XI o |
| IV |  | H$_2$/Pd(OH)$_2$ | XII a |
| | C$_2$H$_5$— | H$_2$/Pd(OH)$_2$ | XII j |
| | C$_4$H$_{10}$— | H$_2$/Pd(OH)$_2$ | XII k |
| |  (H, CH$_3$O) | H$_2$/Pd(OH)$_2$ | XII r |
| V | CH$_3$— | H$_2$/Pd(OH)$_2$ | XIII i |
| | 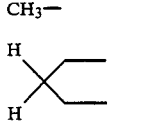 (H,H) | H$_2$/Pd(OH)$_2$ | XIII r |
| |  (O,O ring with CH$_2$—) | H$_2$/Pd(OH)$_2$ | XIII o |
| VI | 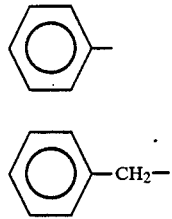 | None | XIV a |
| | —CH$_2$— | None | XIV g |
| | C$_2$H$_5$— | None | XIV j |
| | C$_4$H$_{10}$— | None | XIV k |
| VII |  | H$_2$/Pd(OH)$_2$ | XV a & XVI a** |
| | C$_2$H$_5$— | H$_2$/Pd(OH)$_2$ | XV j & XVI j** |
| | CH$_3$SCH$_2$CH$_2$— | H$_2$/Pd(OH)$_2$ | XV n & XVI n** |
| | 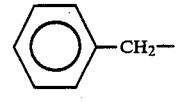 (H,H) | H$_2$/Pd(OH)$_2$ | XV r & XVI r** |
| VIII | —CH$_2$— | aqueous acetic acid or I$_2$/methanol, Δ | XVII g |
| | CH$_3$— | aqueous acetic acid or I$_2$/methanol, Δ | XVII i |
| | C$_4$H$_{10}$— | aqueous acetic acid or I$_2$/methanol, Δ | XVII k |
| | CH$_2$=CHCH$_2$— | aqueous acetic acid or I$_2$/methanol, Δ | XVII m |
| |  | aqueous acetic acid or I$_2$/methanol, Δ | XVII s |
| | OC$_4$H$_{10}$ 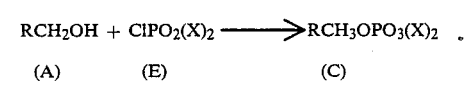—CH$_2$— | aqueous acetic acid or I$_2$/methanol, Δ | XVII t |

*Reagents are commercially available or are synthesized according to K. Sasse (vide supra); L. A. Slotin (vide supra); D. Farquhar, at al., J. Med. Chem., 26, 1153 (1983); F. Ramirez, et al., J. Org. Chem., 48, 2008 (1983). Reagents for mixed esters (R' not equal to R" or R'" not equal to R"") are synthesized using the same methods.
**XV and XVI are separable by chromatography.

Certain of the phosphate esters of Formula I may be prepared according to the following scheme.

$$RCH_2OH + ClPO_2(X)_2 \longrightarrow RCH_3OPO_3(X)_2$$
(A)　　　　(E)　　　　　　　(C)

An alcohol (A) (structures I–VIII, Table I) in anhydrous tetrahydrofuran containing a base such as triethylamine is cooled to −78° C. and treated with a phosphorochloridate (E), (X=a–t, Table I). After 1 hour, the solution is allowed to warm to −10° C. and is then treated with iodine in tetrahydrofuran/water. The volatiles are removed, the residue taken up in dichloromethane/water and chromatographed, debenzylated and purified as described above, giving the bisphosphate esters (c) which refer to structures IX–XVII in Table I.

As an example of the above procedure, a 1 mmol portion of 3,6-anhydro-2-deoxy-4,5-bis-O-(phenylmethyl)-D-manno-heptitol (III, Table I, Ex. 52) is dissolved in 0.3 ml of tetrahydrofuran containing 4 mmol of triethylamine, cooled to −78° C. and treated with 3.5 mmol of diethyl phosphorochloridate (X=j, Table I).

After 1 hour, the solution is allowed to warm to −10° C. over 30 minutes and is then treated with 4 mmol of iodine in a mixture of 0.2 ml of tetrahydrofuran and 0.1 ml of water. The volatiles are removed in vacuo, the residue taken up in dichloromethane/water and then chromatographed, debenzylated and purified as described above, giving product XI j.

Other examples of phosphate esters which can be prepared by the above method are shown in Table IV wherein the structures are identified as in Table I.

TABLE IV

| Alcohol | ClPO$_2$(X)$_2$* X = | Further Steps** | Product |
|---|---|---|---|
| I |  | I$_2$/aqueous THF | IX a |
|  | —CH$_2$— | I$_2$/aqueous THF | IX g |
|  | CH$_3$— | I$_2$/aqueous THF | IX i |
|  | isobutyl— | I$_2$/aqueous THF | IX k |
| II |  | (1) N$_2$O$_4$ (2) H$_2$/Pd(OH)$_2$ | X a |
|  | C$_2$H$_5$— | (1) N$_2$O$_4$ (2) H$_2$/Pd(OH)$_2$ | X j |
|  | isobutyl- | (1) N$_2$O$_4$ (2) H$_2$/Pd(OH)$_2$ | X k |
| III |  | (1) I$_2$/aqueous THF (2) H$_2$/Pd(OH)$_2$ | XI a |
|  | CH$_3$— | (1) I$_2$/aqueous THF (2) H$_2$/Pd(OH)$_2$ | XI i |
|  |  | (1) I$_2$/aqueous THF (2) H$_2$/Pd(OH)$_2$ | XI k |
| IV | C$_2$H$_5$— | (1) N$_2$O$_4$ (2) H$_2$/Pd(OH)$_2$ | XII j |
|  | C$_8$H$_{17}$— | (1) N$_2$O$_4$ (2) H$_2$/Pd(OH)$_2$ | XII k |
| V |  | (1) N$_2$O$_4$ (2) H$_2$/Pd(OH)$_2$ | XIII a |
|  | C$_2$H$_5$— | (1) N$_2$O$_4$ (2) H$_2$/Pd(OH)$_2$ | XIII j |
| VI |  | I$_2$/aqueous THF | XIV a |
|  | —CH$_2$— | I$_2$/aqueous THF | XIV g |

TABLE IV-continued

| Alcohol | ClPO$_2$(X)$_2$* X = | Further Steps** | Product |
|---|---|---|---|
|  | C$_4$H$_{10}$— | I$_2$/aqueous THF | XIV k |
| XVII |  | (1) N$_2$O$_4$ (2) H$_2$/Pd(OH)$_2$ | *** XV a & XVI a |
|  | CH$_3$— | (1) N$_2$O$_4$ (2) H$_2$/Pd(OH)$_2$ | *** XV i & XVI i |
| VIII | —CH$_2$— | (1) I$_2$/aqueous THF (2) aqueous acetic acid | XVIII g |
|  | CH$_3$— | (1) I$_2$/aqueous THF (2) aqueous acetic acid | XVII i |
|  | isopropyl- | (1) I$_2$/aqueous THF (2) aqueous acetic acid | XVII k |

*Reagents are commercially available or are synthesized according to K. Sasse (vide supra); L. A. Slotin (vide supra). Reagents for mixed esters (R' not equal to R" or R'" not equal to R"") are synthesized using the same methods.
**Oxidation is performed according to K. Sasse (vide supra); L. A. Slotin (vide supra); A. S. Jones, et al., J. Chem. Soc. Perkin Trans. I, 199 (1985); C. B. Reese, Tetrahedron, 34, 3143 (1978).
***XV and XVI are separable by chromatography.

Certain of the phosphate esters of Formula I may be prepared according to the following scheme with diazo reagents.

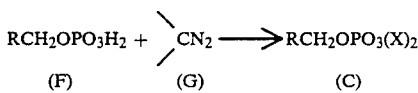

$$\text{RCH}_2\text{OPO}_3\text{H}_2 + \text{CN}_2 \longrightarrow \text{RCH}_2\text{OPO}_3(X)_2$$
$$(F) \qquad (G) \qquad (C)$$

A cold (0°–5° C.) solution of bisphosphate derivative (F), which corresponds to compounds of Formula I where X is hydrogen or products IX–XVII in Table I where X is hydrogen, in anhydrous methanol is treated with a freshly prepared diazo derivative (G). After reaction is complete, any excess reagent is destroyed by the addition of acetic acid, then the volatiles are removed and the product purified by chromatography as described above.

As an example of the above procedure, a cold (0°–5° C.) solution of 1 mmol of bisphosphate XI (Table I, X is hydrogen) in 0.4 ml of anhydrous methanol is treated with freshly prepared diazomethane solution. When the reaction is complete, acetic acid is added to destroy the excess reagent. The volatiles are removed and the product XI j (Table I) is purified by chromatography as described above.

Other examples of phosphate esters which can be prepared by the above method are shown in Table V, wherein the structures are identified as in Table I.

TABLE V

| Bisphosphate | Diazo Reagent* | Product |
|---|---|---|
| IX u | CH$_2$N$_2$ | IX i |
|  | Ph-CHN$_2$ | IX g |
| X u | CH$_3$CHN$_2$ | X j |
| XI u | (CH$_3$)$_2$CN$_2$ | XI k |
|  | Ph-CHN$_2$ | XI g |
| XII u | CH$_2$N$_2$ | XII i |
| XIII u | CH$_3$CHN$_2$ | XIII j |
| XIV u | (CH$_3$)$_2$CN$_2$ | XIV k |
| XV u | Ph-CHN$_2$ | XV g |

TABLE V-continued

| Bisphosphate | Diazo Reagent* | Product |
|---|---|---|
| XVI u | CH₂N₂ | XVI i |
| XVII u | CH₂N₂ | XVII i |
|  | (CH₃)₂CN₂ | XVII k |

*Reagents are freshly prepared according to K. Sasse (vido supra); K. Bruzik and M.-D. Tsai, J. Am. Chem. Soc. 106, 747 (1984); Fieser and Fieser, Reagents for Organic Synthesis, Volumes 1 and 2, Wiley Interscience.

Intermediate alcohols of the type

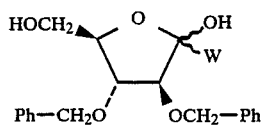

where W is as described in Formula III, can be phosphorylated with chlorophosphates of the formula

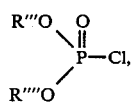

where R''' and R'''' are as described in Formula I (or with ClPO₃(X)₂, where X is as described in Table I), following the procedures of Examples 67, 80 and 83 as set forth below. These compounds can then be deprotected according to Examples 70, 81, 82 and 84 as set forth below to provide the monophosphates of Formula III.

The free acid forms of Formulae I and II (R', R'', R''', R'''' are all hydrogen) can be alkylated using a suitable diazo reagent, such as CH₂N₂, CH₃CHN₂, (CH₃)₂CN₂ or Ph-CHN₂, in anhydrous methanol at 0°–5° C. followed by the addition of acetic acid, evaporation and purification by chromatography, giving tetraesters where each of the ester substitutents are the same in the resulting tetraesters.

The diazo reagents may be prepared and used according to K. Sasse (vide supra); K. Bruzik and M.-D. Tsai, J. Am. Chem. Soc. 106, 747 (1984); or Fieser and Fieser, Reagents For Organic Synthesis, Volumes 1 and 2, Wiley Interscience.

The novel compounds of this invention were tested for their ability to stimulate the enzyme 6-phosphofructo-1-kinase ("PFK") and for their ability to inhibit the enzyme fructose-1,6-bisphosphatase ("FBP") using the procedures described below.

Effects on the activity of PFK were determined using an aldolase-coupled, spectrophotometric assay. The assay mixture contained: 50 mM N-tris(hydroxymethyl)methyl-2-aminoethanesulfonic acid, hydrochloride ("TES-HCl", pH 7.3); 1 mM ethylenediaminetetraacetic acid ("EDTA"); 6 mM magnesium chloride; 2.5 mM dithiothreitol; 0.165 mM nicotinamide adenine dinucleotide ("NADH"); 1 mM adenosine triphosphate ("ATP"); 0.04U aldolase; 0.4U triose phosphate isomerase; 1.5U alpha-glycerolphosphate dehydrogenase; 0.1U of purified rat liver 6-phosphofructo-1-kinase; and various concentrations of the test compound, all in a final volume of 1 ml. The mixture was preincubated for 3 minutes at 30° C. and then the reaction was initiated with 0.2 mM fructose-6-phosphate. The rate of decrease in absorbance at 340 nm was measured at 30° C. with a recording spectrophotometer.

Effects on the activity of FBP were determined using a spectrophotometric assay. The assay mixture contained: 100 mM tris(hydroxymethyl)aminomethane, hydrochloride ("TRIS-HCl", pH 7.4); 2.5 mM beta-mercaptoethanol; 2 mM magnesium chloride; 0.05 mM EDTA; 0.2 mM nicotinamide adenine dinucleotide phosphate ("NADP"); 10 U phosphoglucose isomerase; 5 U glucose-6-phosphate dehydrogenase; 0.02U of purified rat liver FBP; and various concentrations of the test compound, all in a final volume of 1 ml. The mixture was preincubated for 3 minutes at 30° C. and then the reaction was initiated with 0.02 mM fructose-1,6-bisphosphate. The rate of increase in absorbance at 340 nm was measured at 30° C. with a recording spectrophotometer.

The results of these tests on representative compounds of this invention are shown in Table VI.

TABLE VI

| Compound | PFK ED₅₀ (μM) | FBP IC₅₀ (μM) |
|---|---|---|
| Beta-D-fructose-2,6-bisphosphate (control) | 0.02 | 3 |
| 4,7-Anhydro-2,3-dideoxy-D-gluco (and D-manno)-octitol, 1,8-bis (dihydrogen phosphate) | 12.0 | — |
| 2,5-Anhydro-D-glucitol, 1,6-bis(dihydrogen phosphate) | 2.2 | 32 |
| 2,5-Anhydro-D-mannitol, 1,6-bis(dihydrogen phosphate) | 0.26 | 2 |
| 3,6-Anhydro-2-deoxy-D-gluco-heptitol, 1,7-bis(dihydrogen phosphate) | 4.0 | 230 |
| 3,6-Anhydro-2-deoxy-D-manno-heptitol, 1,7-bis(dihydrogen phosphate) | 0.56 | 50 |
| 2,5-Anhydro-2-C-[(phosphonooxy)methyl]-D-glucitol, 6-(dihydrogen phosphate) | 2.0 | — |
| 2,5-Anhydro-2-C-(hydroxymethyl)-D-glucitol, 1,6-bis(dihydrogen phosphate) | 6.3 | — |
| 3,6-Anhydro-2-deoxy-3-C-(hydroxymethyl)-D-manno-heptitol, 1,7-bis(dihydrogen phosphate) | 7.2 | 100 |
| 2,5-Anhydro-D-glycero-D-manno-heptitol, 1,7-bis(dihydrogen phosphate) | 2.1 | — |
| 1-Deoxy-1,1-difluoro-D-fructofuranose, 2,6-bis(dihydrogen phosphate), β-anomer, disodium salt | 0.15 | >800 |
| 1-Deoxy-1,1-difluoro-D-fructofuranose, 2,6-bis(dihydrogen phosphate), α-anomer, disodium salt | 0.05 | >800 |
| 1-Deoxy-1,1-difluoro-D-fructofuranose, 6-(dihydrogen phosphate), sodium salt | 300.00 | 450 |

Although the naturally-occurring control compound had more in vitro activity, the compounds of this invention are more stable, so that they will provide more efficacious control over the glycolytic and gluconeogenic processes in mammals.

The novel compounds of this invention were also tested for their ability to stimulate the enzyme pyrophosphate-dependent 6-phosphofructo-1-kinase ("PPi-PFK"), a growth regulator in plants, using the procedures described below.

Effects on the activity of PPi-PFK were determined using an aldolase-coupled, spectrophotometric assay. The assay mixture contained: 50 mM N-tris(hydroxymethyl)methyl-2-aminoethanesulfonic acid, hydrochloride ("TES-HCl", pH 8.0); 1 mM ethylenediaminetetraacetic acid ("EDTA"); 6 mM magnesium chloride; 2.5 mM dithiothreitol; 0.165 mM nicotinamide adenine dinucleotide ("NADH"); 1 mM fructose-6-phosphate; 0.04U aldolase; 0.4U triose phosphate isomerase; 1.5U alpha-glycerolphosphate dehydrogenase; 0.1U of partially purified potato tuber 6-phosphofructo-1-kinase; and various concentrations of the test compound, all in a final volume of 1 ml. The mixture was preincubated for 3 minutes at 30° C. and then the reaction was initiated with 0.5 mM sodium pyrophosphate. The rate of decrease in absorbance at 340 nm was measured at 30° C. with a recording spectrophotometer.

The results of these tests on representative compounds of this invention are shown in Table VII.

TABLE VII

| Compound | PPi-PFK ED$_{50}$ (μM) |
|---|---|
| Beta-D-fructose-2,6-bisphosphate (control) | 0.004 |
| 2,5-Anhydro-2-C-(hydroxymethyl)-D-glucitol, 1,6-bis(dihydrogen phosphate) | 0.4 |
| 2,5-Anhydro-2-C-[(phosphonooxy)methyl]-D-glucitol, 6-(dihydrogen phosphate) | 6.6 |
| -Deoxy-1,1-difluoro-D-fructofuranose, 2,6-bis(dihydrogen phosphate), β-anomer tetrasodium salt | 0.3 |
| -Deoxy-1,1-difluoro-D-fructofuranose, 2,6-bis(dihydrogen phosphate), α-anomer, tetrasodium salt | 15.0 |
| -Deoxy-1,1-difluoro-D-fructofuranose, 6-(dihydrogen phosphate), sodium salt | 1000.0 |

Although the naturally-occurring control compound had more in vitro activity, the compounds of this invention are more stable, so that they will provide more efficacious control over PPi-PFK in plants.

The significance of this result is as follows. Fructose-2,6-bisphosphate plays an important role in the partitioning of carbon flow between sucrose synthesis in the cytosol and starch synthesis in the chloroplast of plants. Analogs of fructose-2,6-bisphosphate, by activating the pyrophosphate-dependent phosphofructokinase in the cytosol, would reduce sucrose synthesis and favor starch production, which in turn could lead to decreased root growth and to inhibition of reproduction.

The compounds of Formulae I and II are normally administered to mammals in the form of their tetraesters, that is, where R', R'', R''' and R'''' are other than hydrogen. The esters, being more lipophilic than the acids (R', R'', R''', R''''=H), pass through the mammalian cell wall more readily.

When the compounds of the present invention are employed for the above described utility, they may be combined with one or more pharmaceutically acceptable carriers such as solvents, diluents and the like, and may be administered in such forms as tablets, capsules, dispersible powders, granules or suspensions containing, for example, from about 0.5 to 5.0% of suspending agent, syrups containing, for example, from about 10 to 50% of a carrier, and elixirs containing, for example, from about 20 to 50% of ethanol, and the like, or parenterally in the form of sterile injectable solutions or suspensions containing from about 0.5 to 5.0% suspending agent in isotonic medium. These pharmaceutical preparations may contain, for example, from about 0.5 to 90.0% of the active ingredient in combination with the carrier, more usually between 5.0 and 60.0% by weight.

The effective dosage of active ingredient employed may vary depending on the particular compound, the mode of administration and the severity of the conditions being treated. However, in general, satisfactory results are obtained when the compounds of this invention are administered at a daily dosage of from about 1 mg to about 50 mg per kg of body weight, preferably given in divided doses two to four times daily or in sustained release form. Dosage forms suitable for internal use comprise from about 1 mg to about 50 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. The compounds may be administered by a variety of routes including oral, intravenous, intramuscular and subcutaneous. Solid carriers include starch, lactose, dicalcium phosphate, microcrystalline cellulose, and kaolin; while liquid carriers include sterile water, polyethylene glycols, non-ionic surfactants and edible oils such as corn, peanut and sesame oils, as appropriate to the nature of the active ingredient and the particular form of administration desired. Adjuvants customarily employed in the preparation of pharmaceutical compositions may be advantageously included, such as flavoring agents, coloring agents, preservatives and antioxidants, e.g., vitamin E, ascorbic acid, butylated hydroxytoluene, and the like.

The preferred pharmaceutical compositions in terms of ease of preparation are solid compositions, particularly tablets and hard-filled or liquid-filled capsules. Oral administration of the compounds is preferred. These compounds may, however, be administered parenterally or intraperitoneally. Solutions or suspensions of the active compounds can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparations of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a polyol such as glycerol, propylene glycol or liquid polyethylene glycol, suitable mixtures thereof, or vegetable oils.

The invention will be more fully described in conjunction with the following specific examples which are not to be construed as limits thereon.

EXAMPLE 1

3,6-Anhydro-2-deoxy-4,5,7-tris-O-(phenylmethyl)-D-glucoheptitol, and 2,5-Anhydro-6-deoxy-1,3,4-tris-O-(phenylmethyl)-D-manno-heptitol A 2.0 g portion of 50% sodium hydride in oil was washed with hexane and dried. To this was added 40 ml of dry dimethoxyethane and 9.0 g of triethylphosphonoacetate in an ice bath. This reagent was then stirred for 1 hour at room temperature.

An 8.4 g portion of 2,3,5-tris-O-(phenylmethyl)-D-arabinofuranose (Sigma Chemical Co.) was added to the above reagent, the mixture was stirred for 1 day, then poured into ice water and extracted with ether. The extract was dried and then evaporated, giving an oil which was chromatographed on silica gel, eluting with hexane:ethyl acetate (9:1), giving 8.2 g of 2,3-dideoxy-4,5,7-tris-O-(phenylmethyl)-D-arabino-3-heptulo-3,6-furanosonic acid, ethyl ester.

A 4.9 g portion of the above ester was dissolved in 75 ml of dry ether and added dropwise to a slurry of 670 mg of lithium aluminum hydride in 50 ml of ether under argon. After 3 hours, this mixture was treated with 7 ml of saturated aqueous sodium sulfate. The solids were removed by filtration and washed with ether. The combined filtrate and wash was washed with brine, dried and evaporated, giving 4.47 g of the desired mixture of isomers.

EXAMPLE 2

3,6-Anhydro-2-deoxy-4,5,7-tris-O-(phenylmethyl)-D-gluco-heptitol, 1-(diphenyl phosphate), and 3,6-Anhydro-2-deoxy-4,5,7-tris-O-(phenylmethyl)-D-manno-heptitol, 1-(diphenyl phosphate)

A 1.7 g portion of a mixture of 3,6-anhydro-2-deoxy-4,5,7-tris-O-(phenylmethyl)-D-gluco-heptitol and 2,5-anhydro-6-deoxy-1,3,4-tris-O-(phenylmethyl)-D-manno-heptitol was treated with 1.8 g of diphenylphosphorochloridate in 6.5 ml of dry pyridine at 0° C. The mixture was stirred at 0° C. for 1 hour, then at −8° C. overnight. Two drops of water were added and the mixture concentrated in vacuo. The residue was dissolved in dichloromethane, washed with water, cold 1N hydrochloric acid, and saturated aqueous sodium bicarbonate, then dried and evaporated, giving an oil. This oil was flash chromatographed on silica gel eluting with hexane:ether:toluene (1:1:1), giving 2.5 g of the desired mixture of isomers as an oil.

EXAMPLE 3

3,6-Anhydro-2-deoxy-D-gluco-heptitol, 1-(diphenyl phosphate), and 3,6-Anhydro-2-deoxy-D-manno-heptitol, 1-(diphenyl phosphate)

A 2.48 g portion of a mixture of 3,6-anhydro-2-deoxy-4,5,7-tris-O-(phenylmethyl)-D-gluco (and manno)-heptitol, 1-(diphenyl phosphate) was dissolved in a mixture of 50 ml of methanol and 40 ml of glacial acetic acid and hydrogenated at 60 psi over 10% palladium on carbon catalyst overnight. The mixture was filtered and the filtrate evaporated to a yellow oil. This oil was flash chromatographed, eluting with dichloromethane:acetone:methanol (8.5:2.0:0.4).

Fractions containing the mobile isomer were combined and evaporated, giving 550 mg of 3,6-anhydro-2-deoxy-D-gluco-heptitol, 1-(diphenyl phosphate).

Fractions containing the more polar isomer were combined and evaporated, giving 475 mg of 3,6-anhydro-2-deoxy-D-manno-heptitol, 1-(diphenyl phosphate).

EXAMPLE 4

3,6-Anhydro-2-deoxy-D-gluco-heptitol, 1,7-bis(diphenyl phosphate)

A solution of 506 mg of 3,6-anhydro-2-deoxy-D-gluco-heptitol, 1-(diphenyl phosphate) in 3.4 ml of pyridine was cooled in an ice bath and treated with 335 μl of diphenyl phosphorochloridate. The mixture was stirred at 0° C. for 20 minutes and then stored in a freezer for 3 hours. Two drops of water were added, the mixture was warmed to room temperature and concentrated in vacuo. The residue was taken up in dichloromethane, washed with water, cold 1N hydrochloric acid, saturated aqueous sodium bicarbonate, and brine, then dried and evaporated. The resulting oil was flash chromatographed, eluting with 3% methanol in dichloromethane. The fractions were evaporated, giving 274 mg of the desired product, $[\alpha]_D^{26} = +11° \pm 2°$ (c, 0.46 chloroform).

EXAMPLE 5

3,6-Anhydro-2-deoxy-D-gluco-heptitol, 1,7-bis(dihydrogen phosphate)

A 235 mg portion of 3,6-anhydro-2-deoxy-D-gluco-heptitol, 1,7-bis(diphenyl phosphate) was dissolved in 35 ml of methanol and hydrogenated at 60 psi over platinum oxide for 1 hour. The mixture was filtered and the filtrate evaporated, giving 130 mg of the desired product as a colorless oil.

EXAMPLE 6

3,6-Anhydro-2-deoxy-D-manno-heptitol, 1,7-bis(diphenyl phosphate)

A solution of 470 mg of 3,6-anhydro-2-deoxy-D-manno-heptitol, 1-(diphenyl phosphate) in 3 ml of pyridine was cooled in an ice bath, then treated with 292 μl of diphenyl phosphorochloridate and treated as described in Example 4. The fractions were combined and evaporated, giving 388 mg of the desired product, $[\alpha]_D^{26} = +24° \pm 2°$ (c, 0.525, chloroform).

EXAMPLE 7

3,6-Anhydro-2-deoxy-D-manno-heptitol, 1,7-bis(dihydrogen phosphate)

A 320 mg portion of 3,6-anhydro-2-deoxy-D-manno-heptitol, 1,7-bis(diphenyl phosphate) was dissolved in 30 ml of methanol and reacted as described in Example 5, giving 300 mg of the desired product as a colorless oil.

EXAMPLE 8

4,7-Anhydro-2,3-dideoxy-5,6,8-tris-O-(phenylmethyl)-D-gluco-octononitrile, and 4,7-Anhydro-2,3-dideoxy-5,6,8-tris-O-(phenylmethyl)-D-manno-octononitrile A 2.0 g portion of 3,6-anhydro-2-deoxy-4,5,7-tris-O-(phenylmethyl)-D-gluco-heptitol and 2,5-anhydro-6-deoxy-1,3,4-tris-O-(phenylmethyl)-D-manno-heptitol in 20 ml of dry pyridine was treated with 1.3 g of p-toluenesulfonyl chloride at 0° C. The solution was refrigerated overnight, then poured over ice and extracted with ether. The ether extracts were combined, washed with saturated aqueous copper sulfate and brine, dried and evaporated to an oil.

A 1.85 g portion of this oil was dissolved in 15 ml of anhydrous dimethyl sulfoxide and treated with 3.6 mg of sodium cyanide. The mixture was heated at 85°–95° C. for 5.5 hours and then refrigerated overnight. This mixture was poured over a mixture of ice and ammonium chloride and extracted with ether. The combined ether extracts were washed with water and brine, dried and evaporated to an orange oil. This oil was flash chromatographed, eluting with hexane:ethyl acetate (4:1), to afford 834 mg of the desired mixture of isomers.

EXAMPLE 9

4,7-Anhydro-2,3-dideoxy-5,6,8-tris-O-(phenylmethyl)-D-gluco-octitol, and
2,4-Anhydro-6,7-dideoxy-1,3,4-tris-O-(phenylmethyl)-D-manno-octitol A solution of 800 mg of 4,7-anhydro-2,3-dideoxy-5,6,8-tris-O-(phenylmethyl)-D-gluco (and manno)octononitrile in 1.1 ml of ethanol and 300 μl of water was treated with 208 mg of potassium hydroxide. The mixture was heated overnight at 60° C., then neutralized, extracted with ether and the extract evaporated, giving 780 mg of a viscous oil.

This oil was dissolved in 15 ml of ether and added to a solution of 300 mg of lithium aluminum hydride in 10 ml of ether. The mixture was stirred 2.5 hours, heated at reflux for 30 minutes and then 3 ml of saturated aqueous sodium sulfate was added. The solids were removed, washed with ether, the ether solutions combined and evaporated, giving 680 mg of a yellowish oil. This oil was flash chromatographed, eluting 40 ml fractions with hexane:ethyl acetate (2:1). Fractions 9–14 were combined and evaporated, giving 560 mg of the desired mixture of isomers as an oil.

EXAMPLE 10

4,7-Anhydro-2,3-dideoxy-D-gluco-octitol, and
4,7-Anhydro-2,3-dideoxy-D-manno-octitol A 530 mg portion of 4,7-anhydro-2,3-dideoxy-5,6,8-tris-O-(phenylmethyl)-D-gluco-octitol and 2,5-anhydro-6,7-dideoxy-1,3,4-tris-O-(phenylmethyl)-D-manno-octitol was dissolved in 30 ml of methanol:glacial acetic acid (1:1) and hydrogenated at 60 psi for 20 hours over 10% palladium on carbon. The mixture was filtered, the filtrate evaporated and the residue flash chromatographed, eluting with 10% methanol in dichloromethane, giving 200 mg of the desired mixture of isomers as an oil.

EXAMPLE 11

4,7-Anhydro-2,3-dideoxy-D-gluco-octitol,
1,8-bis(diphenyl phosphate), and
4,7-Anhydro-2,3-dideoxy-D-manno-octitol,
1,8-bis(diphenyl phosphate)

A 186 mg portion of 4,7-anhydro-2,3-dideoxy-D-gluco (and manno)-octitol in 3 ml of dry pyridine was treated with 526 μl of diphenyl phosphorochloridate at 0° C. over 10 minutes. The mixture was stored in a freezer overnight, and treated as described in Example 4. The resulting oil was flash chromatographed, eluting with 4% methanol in dichloromethane, giving 390 mg of the desired mixture of isomers as an oil.

EXAMPLE 12

4,7-Anhydro-2,3-dideoxy-D-gluco-octitol,
1,8-bis(dihydrogen phosphate), and
4,7-Anhydro-2,3-dideoxy-D-manno-octitol.
1,8-bis(dihydrogen phosphate)

A 289 mg portion of 4,7-anhydro-2,3-dideoxy-D-gluco (and manno)-octitol, 1,8-bis(diphenyl phosphate) in 25 ml of methanol was hydrogenated at 60 psi for 1.7 hours over platinum oxide. The mixture was filtered and the filtrate evaporated, giving 179 mg of the desired mixture of isomers as an oil.

EXAMPLE 13

2,5-Anhydro-D-glucitol

The title compound was prepared by a modification of the method of T. A. W. Koerner, et al., Carbohydrate Research, 59, 403–416 (1977). Acidic dehydration of D-mannitol and isopropylidenation of the mixture of anhydrides gave a dark syrup. A solution of the syrup in acetone was stirred over potassium carbonate, filtered and evaporated. The desired isopropylidene derivative of anhydroglucitol was isolated by HPLC (silica gel, 28% yield from D-mannitol) without going through the trityl derivative. Hydrolysis of the isopropylidene gave 2,5-anhydro-D-glucitol.

EXAMPLE 14

2,5-Anhydro-1,6-bis-O-(triphenylmethyl)-O-glucitol

A solution of 435 mg of 2,5-anhydro-D-glucitol in 5 ml of pyridine was treated with 1.7 g of trityl chloride for 42 hours. Most of the pyridine was removed in vacuo, then the residue was taken up in dichloromethane and evaporated, giving a gum. This gum was flash chromatographed, eluting with toluene:ether (4:1), giving 820 mg of the desired compound.

EXAMPLE 15

2.5-Anhydro-3,4-bis-O-(phenylmethyl)-1,6-bis-O-(triphenylmethyl)-D-glucitol

A solution of 800 mg of 2,5-anhydro-1,6-bis-O-(triphenylmethyl)-D-glucitol in 16 ml of dry dimethylformamide was treated with 240 mg of freshly washed sodium hydride. The mixture was stirred 1.5 hours, then 1.30 g of benzyl bromide was added and stirring continued for 2.5 days. Methanol was added, the solvents removed in vacuo and the residue taken up in chloroform/water. The organic layer was washed with water and brine, then dried and evaporated, giving a yellow oil which was flash chromatographed, eluting with hexane:ethyl acetate (12:1), giving 847 mg of the desired compound.

EXAMPLE 16

2,5-Anhydro-3,4-bis-O-(phenylmethyl)-D-glucitol

A solution of 847 mg of 2,5-anhydro-3,4-bis-O-(phenylmethyl)-1,6-bis-O-(triphenylmethyl)-D-glucitol in 5 ml of acetone was treated with 16 ml of 80% aqueous acetic acid with stirring for 1 hour at 80° C., for 20 hours at room temperature and then evaporated in vacuo. The residue was taken up in ether, washed with brine, dried and evaporated to an oil. Chromatography of the oil, eluting with ether, gave 260 mg of the desired compound.

EXAMPLE 17

2,5-Anhydro-3,4-bis-O-(phenylmethyl)-D-glucitol,
1,6-bis(diphenyl phosphate)

A 219 mg portion of 2,5-anhydro-3,4-bis-O-(phenylmethyl)-D-glucitol was treated with 410 μl of diphenyl phosphorochloridate in 2 ml of pyridine at 0° C. The mixture was refrigerated overnight, then treated as described in Example 4. The resulting oil was flash chromatographed, eluting with 2.5% methanol in dichloromethane. Evaporation of the fractions gave 481 mg of the desired compound as an oil. Crystallization from hexane/ethyl acetate produced a solid, mp 76°–77.5° C.

EXAMPLE 18

2.5-Anhydro-D-glucitol. 1,6-bis(diphenyl phosphate)

A 428 mg portion of 2,5-anhydro-3,4-bis-O-(phenylmethyl)-D-glucitol, 1,6-bis(diphenyl phosphate) was hydrogenated according to Example 10. Flash chromatography of the resulting oil, eluting with 3% methanol in dichloromethane, gave 192 mg of the desired product.

EXAMPLE 19

2,5-Anhydro-D-glucitol, 1,6-bis(dihydrogen phosphate)

A 180 mg portion of 2,5-anhydro-D-glucitol, 1,6-bis(diphenyl phosphate) in 15 ml of methanol was hydrogenated over platinum oxide for 1.4 hours. Filtration and evaporation of the filtrate gave the desired product as an oil.

EXAMPLE 20

2,5-Anhydro-3,4.6-tris-O-(phenylmethyl)-D-mannose 2,5-Anhydro-D-mannose was made by the procedure of D. A. Otero and R. Simpson, *Carbohydrate Research*, 128, 79–86 (1984).

2,5-Anhydro-D-mannose was dissolved in 400 ml of anhydrous methanol and treated with 18 ml of acetyl chloride. The solution was heated at reflux for 3 hours, then neutralized with lead carbonate, filtered and the filtrate concentrated to an oil which was purified by chromatography, giving 2,5-anhydro-D-mannose, dimethyl acetal.

A 3.14 g portion of the above acetal was dissolved in 120 ml of dry dimethylformamide and treated with 2.46 g of sodium hydride. This suspension was stirred for 1 hour, then 16.6 ml of benzyl bromide was added and stirring continued overnight. A 1.0 ml portion of benzyl bromide was added and stirring continued overnight. The product was purified by chromatography, giving 6.0 g of 2,5-anhydro-3,4,6-tris-O-(phenylmethyl)-D-mannose, dimethyl acetal.

A 790 mg portion of 2,5-anhydro-3,4,6-tris-O-(phenylmethyl)-D-mannose, dimethyl acetal was dissolved in 25 ml of acetonitrile and treated with 3.3 ml of 48% aqueous tetrafluoroboric acid. After 20 minutes, the reaction was quenched with solid sodium bicarbonate. The solvent was removed and the residue extracted with ether. The extract was evaporated, giving a yellow oil. This oil was flash chromatographed, eluting with hexane:ethyl acetate, giving 530 mg of the desired compound.

EXAMPLE 21

3,6-Anhydro-l,2-dideoxy-4,5,7-tris-O-(phenylmethyl)-D-manno-hept-1-enitol

A 1.39 g portion of Tebbe's reagent (F. N. Tebbe et al., *J. Amer. Chem. Soc.*. 100, 3611 (1978)) was dissolved in 11 ml of cold ether ($-40°$ C.) and a cold solution of 1.84 of 2,5-anhydro-3,4,6-tris-O-(phenylmethyl)-D-mannose in 11 ml of ether was added. This mixture was stirred at $-40°$ C. for 15 minutes, $-35°$ to $-25°$ C. for 30 minutes, warmed to room temperature, stirred for 15 minutes, cooled to $-5°$ C. and 1.5 ml of 15% aqueous sodium hydroxide added. The mixture was stirred at room temperature until effervescence stopped, then 215 ml of ether was added and the mixture filtered. The filtrate was evaporated and the residual oil flash chromatographed, eluting with hexane:ethyl acetate (15:1). The fractions were combined and evaporated, giving 650 mg of the desired compound.

EXAMPLE 22

2,5-Anhydro-1,3,4-tris-O-(phenylmethyl)-D-glycero-D-manno-heptitol

A 1.05 g portion of 3,6-anhydro-1,2-dideoxy-4,5,7-tris-O-(phenylmethyl)-D-manno-hept-1-enitol was dissolved in 14 ml of dry pyridine and treated with a solution of 748 mg of osmium tetroxide in 4 ml of pyridine. The mixture was stirred 2¼ hours and then treated with a solution of 1.35 g of sodium bisulfite, 22.5 ml of water and 15 ml of pyridine. After 30 minutes, the mixture was extracted three times with dichloromethane:chloroform (1:1). The organic phases of the extracts were combined, washed with water, 1N hydrochloric acid, water, then brine, dried and evaporated to a greenish oil. This oil was flash chromatographed, eluting with hexane:ether (1:2), then (1:3) and finally with ether. The fractions were combined and evaporated, giving 680 mg of the major, more mobile isomer as a white solid.

EXAMPLE 23

2,5-Anhydro-1,3,4,6,7-pentakis-O-(phenylmethyl)-D-glycero-D-manno-heptitol

An 850 mg portion of 2,5-anhydro-1,3,4-tris-O-(phenylmethyl)-D-glycero-D-manno-heptitol was dissolved in dry dimethylformamide and added to a slurry of 218 mg of sodium hydride in dimethylformamide. After stirring 1 hour, 1.9 ml of benzyl bromide was added, the mixture stirred overnight, 5 ml to methanol added and the solvents evaporated. The residue was taken up in 50 ml of water and 50 ml of dichloromethane, the organic layer separated, washed with water and brine, dried and evaporated to an orange oil. This oil was flash chromatographed, eluting with hexane:ether (5:1). Evaporation of the fractions gave 1.06 g of the desired compound.

EXAMPLE 24

2,5-Anhydro-3,4,6-tris-O-(phenylmethyl)-D-glycero-D-manno-heptitol, 1,7-diacetate A 750 mg portion of 2,5-anhydro-1,3,4,6,7-pentakis-O-(phenylmethyl)-D-glycero-D-manno-heptitol was dissolved in 2 ml of cold acetic anhydride and then treated with 50 $\mu$l of borontrifluoride etherate. After 15 minutes, the reaction was quenched with 1.5 ml of saturated aqueous sodium bicarbonate and then evaporated. The residue was taken up in ether:water (1:1). The ether layer was washed with brine, dried and evaporated. The residual oil was flash chromatographed, with hexane:ethyl acetate (5:1). The fractions were combined and evaporated, giving 606 mg of the desired compound.

EXAMPLE 25

2,5-Anhydro-3,4,6-tris-O-(phenylmethyl)-D-glycero-D-manno-heptitol

A solution of 485 mg of 2,5-anhydro-3,4,6-tris-O-(phenylmethyl)-D-glycero-D-manno-heptitol 1,7-diacetate in 2 ml of ethanol was treated with 183 $\mu$l of an ethanolic solution of sodium ethoxide (2.4N). After 1 hour, 150 $\mu$l of glacial acetic acid was added and the mixture evaporated. The residue was taken up in ether, washed with saturated aqueous sodium bicarbonate and brine, dried and evaporated. Flash chromatography, eluting with hexane:ethyl acetate (1:1), gave 290 mg of the desired compound.

EXAMPLE 26

2,5-Anhydro-3,4,6-tris-O-(phenylmethyl)-D-glycero-D-manno-heptitol, 1,7-bis(diethyl phosohate)

A solution of 267 mg of 2,5-anhydro-3,4,6-tris-O-(phenylmethyl)-D-glycero-D-manno-heptitol in 1.5 ml of pyridine was cooled in an ice bath and treated with 280 μl of diethyl phosphorochloridate. The mixture was refrigerated overnight, then 100 μl of water was added, the mixture stirred 15 minutes and then evaporated. The residue was taken up in ether, washed with water, cold 1N hydrochloric acid, saturated aqueous sodium bicarbonate and brine, dried and evaporated. The residual oil was flash chromatographed, eluting with 2% methanol in dichloromethane, giving 163 mg of the desired compound.

EXAMPLE 27

2,5-Anhydro-3,4.6-tris-O-(phenylmethyl)-D-glycero-D-manno-heptitol, 1,7-bis(dihydrogen phosphate)

A 148 mg portion of 2,5-anhydro-3,4,6-tris-O-(phenylmethyl)-D-glycero-D-manno-heptitol, 1,7-bis(diethyl phosphate) was dissolved in 1 ml of deuterated chloroform under argon. A 166 μl portion of bromotrimethyl silane was added, the mixture stirred 4 hours and then refrigerated 48 hours. The solution was evaporated and the residue evaporated twice from a mixture of 1 ml of acetone and 9 μl of water, giving 135 mg of the desired compound as an oil.

EXAMPLE 28

2.5-Anhydro-D-glycero-D-manno-heptitol, 1,7-bis(dihydrogen phosphate)

A solution of 128 mg of 2,5-anhydro-3,4,6-tris-O-(phenylmethyl)-D-glycero-D-manno-heptitol, 1,7-bis(dihydrogen phosphate) in 25 ml of methanol was hydrogenated over 10% palladium on carbon for 7.5 hours and then filtered. The filtrate was evaporated, giving 78 mg of the desired product.

EXAMPLE 29

2,5-Anhydro-1,3.4-tris-O-0-(phenylmethyl)-D-mannitol

A 5.68 g portion of 2,5-anhydro-3,4,6-tris-O-(phenylmethyl)-D-mannose (prepared in accordance with Example 20) was dissolved in 50 ml of anhydrous ether and this solution was added to a slurry of 1 g of lithium aluminum hydride in 50 ml of ether under argon in an ice bath. This mixture was stirred at reflux for 1.75 hours, then 10 ml of saturated aqueous sodium sulfate was added. The solids were removed, washed with ether and the ether solutions combined and evaporated. Chromatography, eluting with hexane:ethyl acetate (3:1), gave 4.79 g of the desired compound.

EXAMPLE 30

2,5-Anhydro-D-mannitol

A 1.96 g portion of 2,5-anhydro-1,3,4-tris-O-(phenylmethyl)-D-mannitol was hydrogenated as described in Example 10. The residual oil was flash chromatographed, with 10% methanol in dichloromethane, giving 670 mg of the desired compound.

EXAMPLE 31

2,5-Anhydro-D-mannitol, 1,6-bis(diphenyl phosohate)

A 520 mg portion of 2,5-anhydro-D-mannitol was dissolved in 8 ml of dry pyridine at 0° C. and then treated with 2.20 g of diphenyl phosphorochloridate over 5 minutes. This mixture was stored in a freezer overnight, then treated as described in Example 4. The resulting oil was flash chromatographed, eluting with ether:hexane (4:1), then ether, then 2% methanol in ether and finally 3% methanol in ether. The fractions containing the more polar material were evaporated, giving 850 mg of the desired product.

EXAMPLE 32

2,5-Anhydro-D-mannitol, 1,6-bis(dihydrogen phosphate)

A 520 mg portion of 2,5-anhydro-D-mannitol, 1,6-bis(diphenyl phosphate) was hydrogenated according to Example 5, giving 300 mg of the desired product as a glassy oil.

EXAMPLE 33

2,5-Anhydro-2-C-(hydroxymethyl)-3,4,6-tris-O-(phenylmethyl)-D-glucitol

A 1 177 g portion of 2,5-anhydro-3,4,6-tris-O-(phenylmethyl)-D-mannose (prepared in accordance with Example 20) was dissolved in 8.5 ml of methanol and then treated with 5.11 ml of 37% formalin and 480 mg of potassium carbonate. This mixture was heated under argon at 85° C. for 4 hours, then cooled, neutralized with 10% sulfuric acid and evaporated. The residue was taken up in chloroform, washed with brine and evaporated. The residual oil was flash chromatographed, eluting with hexane:ethyl acetate (3:2). The combined fractions gave 860 mg of the desired product, $[\alpha]_D^{26} = +37° \pm 2$ (c. 0.555, chloroform).

EXAMPLE 34

2-C-[(Acetyloxy)methyl]-2,5-anhydro-3,4-bis-O-(phenylmethyl)-D-glucitol, 1,6-diacetate A 2.39 g portion of 2,5-anhydro-2-C-(hydroxymethyl)-3,4,6-tris-O-(phenylmethyl)-D-glucitol was dissolved in 15 ml of acetic anhydride and the solution cooled in an ice bath. A 60 μl portion of borontrifluoride etherate was added dropwise and the mixture was stirred at 0° C. for 40 minutes. A 10 ml portion of saturated aqueous sodium bicarbonate was added, the mixture was stirred at 0° C. for 15 minutes, then at room temperature for 15 minutes and concentrated in vacuo. The residue was taken up in ether/water, the ether layer washed with brine, dried and evaporated. The residual oil was flash chromatographed, eluting with hexane:ethyl acetate (4:1), giving 1 3.0 g of the desired compound.

EXAMPLE 35

2,5-Anhydro-2-C-(hydroxymethyl)-3,4-bis-O-(phenylmethyl)-D-glucitol

A 1.7 g portion of 2-C-[(acetyloxy)methyl]-2,5-anhydro-3,4-bis-O-(phenylmethyl)-D-glucitol, 1,6-diacetate was treated with 1.6 g of potassium carbonate, 10 ml of water and 8.5 ml of methanol and the mixture heated at reflux for 40 minutes and then evaporated. The residue was taken up in ether/water. The water layer was extracted twice with ether. All ether layers were combined, washed with brine, dried and evaporated. The residual oil was flash chromatographed, eluting with 4% methanol in dichloromethane, giving 1.0 g of the desired compound.

EXAMPLE 36

[R]-2,5-Anhydro-2-C-(hydroxymethyl)-3,4-bis-O-(phenylmethyl)-1,2¹-O-(phenylmethylene)-D-glucitol mixture with
[S]-2,5-Anhydro-2-C-(hydroxymethyl)-3,4-bis-O-(phenylmethyl)1,2¹-O-(phenylmethylene)-D-glucitol A 1.1 g portion of 2,5-anhydro-2-C-(hydroxymethyl)-3,4-bis-O-(phenylmethyl)-D-glucitol, 568 μl of benzaldehyde dimethyl acetal, 2 ml of dry dimethylformamide and 10 mg of p-toluenesulfonic acid were combined and heated at 60° C. under reduced pressure for 1 hour. A 0.5 ml portion of dry dimethylformamide and 50 μl of benzaldehyde dimethyl acetal were added, the mixture stirred at 60° C. for 30 minutes, then at 65° C. for 30 minutes and finally at 90° C. to remove the solvent. The residue was dissolved in chloroform, saturated aqueous sodium bicarbonate was added, and the layers separated. The chloroform layer was washed with brine and dried. The solids were filtered and the filtrate evaporated, giving 1.3 g of the desired compounds as a mixture of diastereomers.

EXAMPLE 37

2,5-Anhydro-2-C-[(phenylmethoxy)methyl]-3,4-bis-O-(phenylmethyl)-D-glucitol mixture with
2,5-anhydro-2-C-(hydroxymethyl)-1.3,4-tris-O-(phenylmethyl)-D-glucitol A 760 mg portion of a mixture of [R and S]-2,5-anhydro-2-C-(hydroxymethyl)-3,4-bis-O-(phenylmethyl)-1,2¹-O-(phenylmethylene)-D-glucitol was dissolved in 6 ml of ether:dichloromethane (1:1) and added to a slurry of 670 mg of aluminum chloride and 194 mg of lithium aluminum hydride in 11 ml of the same solvent under an argon atmosphere. After effervescence subsided, the mixture was heated at 45° C. for 15 minutes, then the reaction was quenched by the addition of 2.7 ml of ethyl acetate and 5.4 ml of water. Work-up with ether gave 730 mg of the desired compounds as a mixture

EXAMPLE 38

2.5-Anhydro-2-C-[(phenylmethoxy)methyl]-3,4-bis-O-phenylmethyl)-D-glucitol, 1,6-bis(diphenyl phosphate) mixture with
2,5-Anhydro-2-C-[[diphenoxyphosphinyl)oxy]methyl]1,3,4-tris-O-(phenylmethyl)-D-glucitol, 6-(diphenyl phosphate)

A 730 mg portion of 2,5-anhydro-2-C-[(phenylmethoxy)methyl]-3,4-bis-O-(phenylmethyl)-D-glucitol mixture with 2,5-anhydro-2-C-(hydroxymethyl)-3,4-bis-O-(phenylmethyl)-D-glucitol was dissolved in 4.5 ml of pyridine, then cooled in an ice bath and treated with 1.02 ml of diphenylphosphorochloridate. After 1 hour at 0° C. the mixture was refrigerated overnight, then warmed to room temperature, quenched with water and evaporated. Work-up as in Example 2 gave an oil which was purified by flash chromatography, eluting with 1% methanol in dichloromethane. Evaporation of the fractions gave 1.39 g of the desired compounds as a mixture.

EXAMPLE 39

2,5-Anhydro-2-C-(hydroxymethyl)-D-glucitol, 1,6-bis(diphenyl phosphate)

A 1.36 g portion of 2,5-anhydro-2-C-[(phenylmethoxy)methyl]-3,4-bis-O-(phenylmethyl)-D-glucitol, 1,6-bis(diphenyl phosphate) mixture with 2,5-anhydro-2-C-[[(diphenoxyphosphinyl)oxy]methyl]-1,3,4-tris-O-(phenylmethyl)-D-glucitol, 6-(diphenyl phosphate) was hydrogenated as described in Example 3. Chromatography, eluting with 3% methanol in dichloromethane, gave 330 mg of the more polar desired product.

EXAMPLE 40

2,5-Anhydro-2-C-(hydroxymethyl)-D-glucitol, 1,6-bis(dihydrogen phosohate)

A 330 mg portion of 2,5-anhydro-2-C-(hydroxymethyl)-D-glucitol, 1,6-bis(diphenyl phosphate) in methanol was hydrogenated as in Example 5, giving 238 mg of the desired product.

EXAMPLE 41

2,5-Anhydro-2-C-(hydroxymethyl)-D-glucitol

A 700 mg portion of 2,5-anhydro-2-C-(hydroxymethyl)-3,4,6-tris-O-(phenylmethyl)-D-glucitol prepared in accordance with Example 33 was hydrogenated as described in Example 3, giving a yellow oil. This oil was flash chromatographed, eluting with 15% methanol in dichloromethane, giving 233 mg of the desired compound $[\alpha]_D^{26} = +34° \pm 2$ (c, 0.475, methanol).

EXAMPLE 42

2,5-Anhydro-2-C-(hydroxymethyl)-2¹,3-O-(1-methylethylidene)-D-glucitol

A 225 mg portion of 2,5-anhydro-2-C-(hydroxymethyl)-D-glucitol was treated with 6 ml of dry acetone, 600 mg of copper sulfate and 6 μl of concentrated sulfuric acid. This mixture was stirred 48 hours, then the solids were filtered and washed with acetone. The combined acetone solutions were neutralized with sodium carbonate. After 1 hour, the solids were filtered and washed with acetone. The combined acetone solutions were concentrated in vacuo. The residual oil was chromatographed, eluting with 4% methanol in dichloromethane. The fractions were combined and evaporated, giving 195 mg of the desired compound, $[\alpha]_D^{26} = +44° \pm 4$ (c, 0.31, acetone).

EXAMPLE 43

2,5-Anhydro-2-C-[[(diphenoxyphosphinyl)oxy]methy]-1,3-O-(1-methylethylidene)-D-glucitol, 6-(diphenyl phosohate)

A 1.1 g portion of 2,5-anhydro-2-C-(hydroxymethyl)-2¹,3-O-(1-methylethylidene)-D-glucitol was dissolved in 12 ml of pyridine, gradually cooled to 0° C. and then treated with 3.26 g of diphenyl phosphorochloridate, as in Example 2. The residual oil was flash chromatographed, eluting with ether:hexane (3:1). The fractions containing the more polar product were combined and evaporated, giving 570 mg of the desired compound.

EXAMPLE 44

2,5-Anhydro-2-C-[(phosphonooxy)methyl]-D-glucitol, 6-(dihydrogen phosphate)

A 300 mg portion of 2,5-Anhydro-2-C-[[(diphenoxyphosphinyl)oxy]methyl]-1,3-O-(1-methylethylidene)-D-glucitol, 6-diphenyl phosphate) in methanol was hydrogenated over platinum oxide as described in Example 5, giving the desired product as an oil.

EXAMPLE 45

4,7-Anhydro-4-C-[(benzoyloxy)methyl]-1,2,3-trideoxy-D-arabino-oct-1-enitol, 5,6,8-tribenzoate To a stirred solution of 70.1 g of D-fructofuranose, pentabenzoate [P. Brigl and W. Schinle, *Ber.*, 66, 325–330 (1933)], and 50 ml of allyltrimethylsilane in 1.5 liters of acetonitrile at 0° C., was added 14.0 ml of borontrifluoride etherate, during 2 minutes. This mixture was stirred at 25° C. for 22 hours and then partitioned with ethyl acetate:hexane (2:1) and aqueous sodium bicarbonate. The organic layer was separated, washed well with water and brine, dried and concentrated, giving the desired compound as syrup, PMR $\delta$ 2.78 (2H,d, —CH$_2$CH=).

EXAMPLE 46

4,7-Anhydro-1,2,3-trideoxy-4-C-(hydroxymethyl)-D-manno-oct-1-enitol

To a stirred mixture of 19.9 g of 4,7-anhydro-4-C-[(benzoyloxy)methyl]-1,2,3-trideoxy-D-arabino-oct-1-enitol, 5,6,8-tribenzoate and 450 ml of methanol was added 8.64 g of sodium methoxide in one portion. The resulting solution was stirred at 25° C. for 2 hours and then treated with 100 ml of Dowex® 50W(H+) ion exchange resin. After filtration of the resin, the filtrate was concentrated and the residue partitioned with petroleum ether and water. The water phase was evaporated giving the desired compound as a syrup; single spot on TLC ethyl acetate:methanol:acetic acid (30:10:3), Rf=0.77.

EXAMPLE 47

4$^1$,5:4,7-Dianhydro-1,2,3-trideoxy-4-C-[(1-hydroxy-1methylethoxy)methyl]-6,8-bis-O-(phenylmethyl)-D-manno-oct-1-enitol A mixture of 7.0 g of 4,7-anhydro-1,2,3-trideoxy-4-C-(hydroxymethyl)-D-manno-oct-1-enitol, 10 g of anhydrous copper sulfate, 0.4 ml of concentrated sulfuric acid and 250 ml of acetone was stirred at 25° C. for 17 hours, then cooled to 0° C. and filtered. The filtrate was stirred with 25 ml of 3N sodium hydroxide until neutral and then concentrated. The residue was extracted with dichloromethane. The extract was washed with a minimal amount of water, then concentrated to an oil. This oil was dissolved in 22 ml of dimethylformamide and added to a stirred mixture of 1.44 g of sodium hydride and 10 ml of dimethylformamide at 0° C. This mixture was stirred and treated dropwise with 17.1 g of benzyl bromide. After 20 hours at 25° C., the mixture was cooled to 0° C., quenched with methanol and evaporated under high vacuum. The residue was partitioned with dichloromethane/water. The organic layer was dried and concentrated. The residue was subjected to column chromatography (heptane:ethyl acetate), giving the desired compound as a syrup; PMR of $\delta$ 1.27 and 1.30 (each 3H,s,CH$_3$) and 7.30 (10H,s,aromatic H).

EXAMPLE 48

1,4-Dianhydro-2-deoxy-3-C-[(1-hydroxy-1-methylethoxy)methy]5.7-bis-O-(phenylmethyl)-D-manno-heptitol A stirred solution of 5.5 g of 4$^1$,5:4,7-dianhydro-1,2,3-trideoxy-4-C-[(1-hydroxy-1-methylethoxy) methyl]-6,8-bis-O-(phenylmethyl)-D-manno-oct-1-enitol, 1.3 ml of pyridine and 65 ml of dichloromethane was subjected to ozonolysis at −78° C. The solution was then purged free of ozone and treated with 1.23 g of sodium borohydride and 65 ml of ethanol at −78° C. The mixture was warmed slowly to 25° C., stirred for 18 hours, treated with 80 ml of 1N sodium hydroxide and evaporated free of ethanol. The residue was extracted with ether. The extract was washed with water and brine, dried and concentrated. The residue was subjected to column chromatography on silica gel, eluting with heptane:ethyl acetate to give the desired compound as an oil, CMR $\delta$ 35.6 (CCH$_2$C) and 58.5 (CH$_2$OH).

EXAMPLE 49

3,6:3$^1$,4-Dianhydro-2-deoxy-3-C-[(1-hydroxy-1-methylethoxy)methy]-D-manno-heptitol A mixture of 3.8 g of 3,6:3$^1$,4-dianhydro-2-deoxy-3-C-[(1-hydroxy-1-methylethoxy)methyl]-5,7-bis-O-(phenylmethyl)-D-manno-heptitol, 130 ml of methanol and 30 ml of acetic acid was hydrogenated as described in Example 3. The residue was subjected to column chromatography on silica gel (ethyl acetate:methanol:triethylamine), giving the desired compound as a syrup, CMR $\delta$ 62.2 (s, C-7).

EXAMPLE 50

3,6:3$^1$,4-Dianhydro-2-deoxy-3-C-[(1-hydroxy-1-methylethoxy)methyl]-D-manno-heptitol, 1,7-bis(diphenyl phosohate)

To a stirred solution of 2.26 g of 3,6:3$^1$,-4-dianhydro-2-deoxy-3-C-[(1-hydroxy-1-methylethoxy) methyl]-D-manno-heptitol in 27 ml of pyridine at 0° C., was added 5.4 g of diphenyl phosphorochloridate during 3 minutes. After 5 hours at 0° C., the mixture was treated with 4.5 ml of water, then stirred at 25° C. for 1 hour and partitioned with ether and water. The organic layer was washed with water and brine, dried and concentrated. The residue was subjected to column chromatography on silica gel (ethyl acetate:heptane:acetic acid), giving the desired compound as a syrup, CMR $\delta$ 65.1 (d $^2$J$_{POC}$=5.9 Hz, C-1) and 69.0 (d, J$_{POC}$=6.2 Hz, C-7).

EXAMPLE 51

3,6-Anhydro-2-deoxy-3-C-(hydroxymethyl)-D-manno-hepitol, 1,7-bis(dihydrogen phosphate)

A mixture of 1.68 g of 3,6:3$^1$,4-dianhydro-2-deoxy-3-C-[(1-hydroxy-1-methylethoxy)methyl]-D-manno-heptitol, 1,7-bis(diphenyl phosphate), 0.12 g of platinum oxide and 100 ml of methanol was hydrogenated at 25° C. under an initial pressure of 55 psi. After 4.5 hours, the catalyst was removed by filtration. The filtrate was concentrated, the residue dissolved in water, filtered and concentrated at 25° to 35° C., giving the desired product as a syrup, CMR $\delta$ 61.5 (d, $^2$J$_{POC}$=4.2 Hz, C-1), 62.8 (s, CH$_2$OH) and 64.5 (d, J$_{POC}$=4.0 Hz, C-7).

EXAMPLE 52

3,6-Anhydro-2-deoxy-4,5-bis-O-(phenylmethyl)-D-manno-heptitol, and 3,6-Anhydro-2-deoxy-4,5-bis-O-(phenylmethyl)-D-gluco-heptitol A cold (0°–5° C.) solution of 12.2 g of a mixture of 3,6-anhydro-2-deoxy-4,5,7-tris-O-(phenylmethyl)-D-gluco-heptitol and 2,5-anhydro-6-deoxy-1,3,4-tris-O-(phenylmethyl)-D-manno-heptitol in 64 ml of acetic anhydride was treated with 370 µl of borontrifluoride etherate under argon. After 1¾ hours, 53 ml of saturated aqueous sodium bicarbonate was added, the mixture was stirred at 0° C. for 15 minutes, then at ambient temperature for 15 minutes and the volatiles removed. The residue was taken up in ether/water. The organic layer was separated, dried and evaporated. The residue was taken up in 74 ml of methanol, a solution of 15.4 g of potassium carbonate in 90 ml of water added and this mixture stirred at reflux for 45 minutes. The volatiles were removed, the residue taken up in ether/water and the organic layer separated and evaporated. The 12 g of residue was purified by high pressure liquid chromatography on silica gel, eluting first with hexane:ethyl acetate (1:1), and then with hexane:ethyl acetate (1:3), giving 3,6-anhydro-2-deoxy-4,5-bis-O-(phenylmethyl)-D-gluco-heptitol in 20% yield and 3,6-anhydro-2-deoxy-4,5-bis-O-(phenylmethyl)-D-manno-heptitol in 65% yield.

EXAMPLE 53

2 5-Anhydro-2-C-[[(diphenoxyphosphinyl)oxy]methy]-D-glucitol, 6-(diphenyl phosphate)

A 224 mg portion of 2-C-[[(diphenoxyphosphinyl)oxy]methyl]-1,3-O-(1-methylethylidene)-D-glucitol, 6-(diphenyl phosphate) was treated with 8 ml of 80% aqueous acetic acid at 80° C. for 30 minutes, then cooled and the solvent removed, giving a yellow oil. This oil was flash chromatographed, eluting 25 ml fractions with ether:ethyl acetate (3:1). Fractions 13-25 were combined and evaporated, giving 112 mg of the desired $[\alpha]_D^{26} = +29° +2$ (c, 0.495, chloroform).

EXAMPLE 54

3,6-Anhydro-2-deoxy-D-manno-heptitol, 1,7-bis(2-methoxyethyl phenyl phosphate)

A 1 mmol portion of 3,6-anhydro-2-deoxy-4,5-bis-O-(phenylmethyl)-D-manno-heptitol in 1.5 ml of pyridine is added to a freshly prepared solution of 2 mmol of 2-methoxyethyl phenyl phosphorochloridate in dichloromethane under an argon atmosphere. The mixture is stirred overnight, worked-up as described in Example 2 and then chromatographed giving an oil. This oil is dissolved in 20 ml of methanol and hydrogenated in a Parr apparatus at 60 psi initial pressure using palladium on carbon as catalyst. Filtration and removal of the solvent gives the desired product.

EXAMPLE 55

3-(Hexadecyloxy)-2-methoxypropyl phenyl phosphorochloridate

A 1 mmol portion of 3-(hexadecyloxy)-2-methoxy propanol is added to a 0°–5° C. solution of 1 mmol of phenyl dichlorophosphate in 2 ml of anhydrous dichloromethane containing 1.2 mmol of triethylamine. The mixture is stirred under argon for 1 hour at 5° C., then for 2.5 hours at room temperature and then used as is.

EXAMPLE 56

3,6-Anhydro-2-deoxy-D-manno-heptitol, 1-(2-methoxyethyl, 1-methyl phosphate). 7-(3-[hexadecyloxy1-2-methoxyproyl phenyl phosohate)

A 2 mmol portion of 3,6-anhydro-2-deoxy-4,5,7-tris-O-(phenylmethyl)-D-gluco and D-manno-heptitol mixture is phosphorylated as described in Example 2, using 2 mmol of freshly prepared 2-methoxyethyl methyl phosphorochloridate reagent in dichloromethane. The mixture is stirred overnight. Work-up gives an oil which is purified by chromatography and then hydrogenated over palladium hydroxide catalyst. The resulting mixture of isomers is separated by chromatography.

The isolated 3,6-anhydro-2-deoxy-D-manno-heptitol, 1-(2-methoxyethyl methyl phosphate) is phosphorylated as described in Example 4, using freshly prepared 3-(hexadecyloxy)-2-methoxypropyl phosphorochloridate reagent. Stirring overnight followed by work-up affords the desired tetraester.

EXAMPLE 57

2-Deoxy-2,2-difluoro-4,5,7-tris-O-(phenylmethyl)-D-arabino-3-heptulofuranosonic acid, ethyl ester To a stirred, refluxing suspension of 6.36 g of zinc dust in 75 ml of tetrahydrofuran was added acetate [E. A. Hallinan & J. Fried, *Tetrahedron Letters*, 25, 2301–2302 (1984)] and 20.9 g of 2,3,5-tris-O-(phenylmethyl)-D-arabinonic acid-oamma-lactone [Y. Rabinsohn & H. G. Fletcher, *J. Org. Chem.*, 32, 3452–3457 (1967)] in 175 ml of tetrahydrofuran during 2 hours. After the addition, the mixture was refluxed for 1.5 hours, cooled, and partitioned with ether and 0.2N hydrochloric acid. The organic layer was washed with water, sodium bicarbonate solution, and brine, dried and concentrated. The residue was subjected to column chromatography on silica gel to provide an oil, CMR δ 100.7 (triplet, J=29 Hz, anomeric carbon).

EXAMPLE 58

2-Deoxy-2,2-difluoro-4,5-bis-O-(phenylmethyl)-D-arabino-3-heptulofuranosonic acid, ethyl ester diacetate To a stirred solution of 2.40 g of 2-deoxy-2,2-difluoro-4,5,7-tris-O-(phenylmethyl)-D-arabino-3-heptulofuranosonic acid, ethyl ester in 8.8 ml of acetic anhydride at 0° C. was added 1.08 ml of boron trifluoride etherate. After 2 hours at 0° C., the solution was diluted with ether and stirred with aqueous sodium bicarbonate solution. The organic layer was washed with water and brine, dried, and concentrated. The residue was subjected to column chromatography on silica gel to give an oil, CMR δ 20.7 and 215 (singlets, CH₃CO).

EXAMPLE 59

2-Deoxy-2,2-difluoro-4,5-bis-O-(phenylmethyl)-D-arabino-3-heptulofuranosonic acid, ethyl ester To a stirred solution of 1.83 g of 2-deoxy-2,2-difluoro-4,5-bis-O-(phenylmethyl)-D-arabino-3-heptulofuranosonic acid, ethyl ester diacetate in 5.1 ml of ethanol was added 3.4 ml of 1.5M sodium ethoxide in ethanol at 25° C. After 1.5 hours, the mixture was treated with 0.61 ml of glacial acetic acid and partitioned with ether and water. The organic layer was washed with water, sodium bicarbonate solution, and brine, dried and concentrated. The residue was subjected to column chromatography on silica gel to give an oil; CMR δ 100.1 (triplet, J=29.6 Hz, anomeric carbon)

EXAMPLE 60

2-Deoxy-2,2-difluoro-4,5-bis-O-(phenylmethyl)-D-arabino-3-heptulofuranosonic acid, ethyl ester, 7-(diphenylphosphate)

To a stirred solution of 1.20 g of 2-deoxy-2,2-difluoro-4,5-bis-O-(phenylmethyl)-D-arabino-3-heptulofuranosonic acid, ethyl ester in 8.0 ml of pyridine at 0° C. was added 1.37 ml of diphenylphosphoryl chloride. The resulting mixture was stirred at 0° C. for 2 hours, warmed to 25° C., treated with 2.1 ml of water, stirred at 25° C. for 45 minutes, and partitioned with ether and water. The organic layer was washed with water and brine, dried, and concentrated to give an oil; CMR δ 67.6 (doublet, J=5.2 Hz, $\underline{C}H_2OP$).

EXAMPLE 61

2-Deoxy-2,2-difluoro-4,5-bis-O-(phenylmethyl)-D-arabino-3-heptulofuranosonic acid, ethyl ester, bis(diphenyl phosphate), β-anomer To a stirred solution of 1.31 g of 2-deoxy-2,2-difluoro-4,5-bis-O-(phenylmethyl)-D-arabino-3-heptulofuranosonic acid, ethyl ester, 7-(diphenyl phosphate) and 0.57 g of dimethylaminopyridine in 9.6 ml of dichloromethane and 1.91 ml of pyridine was added 2.37 ml of diphenylphosphoryl chloride, and the resulting mixture was stirred at 25° C. for 18 hours, cooled to 0° C., and treated with 0.42 ml of water. The mixture was stirred at 25° C. for 15 minutes and partitioned with dichloromethane and water. The organic layer was washed with water, cold 0.5N hydrochloric acid, sodium bicarbonate solution, and water, dried and concentrated. The residue was subjected to column chromatography on silica gel (dichloromethane-ether) to give the mobile β-anomer, CMR δ 105.2 (multiplet, anomeric carbon).

EXAMPLE 62

2-Deoxy-2,2-difluoro-4,5-bis-O-(phenylmethyl)-D-arabino-3-heptulofuranosonic acid, ethyl ester, bis(diphenylohosphate), α-anomer In the manner of Example 61, treatment of 2-deoxy-2,2-difluoro-4,5-bis-O-(phenylmethyl)-D-arabino-3-heptulofuranosonic acid, ethyl ester, 7-(diphenyl phosphate) with diphenylphosphoryl chloride in the presence of dimethylaminopyridine followed by chromatography on silica gel gave the polar α-anomer as a syrup, CMR δ 107.5 (multiplet, anomeric carbon).

EXAMPLE 63

2-Deoxy-2,2-difluoro-4,5,7-tris-O-(phenylmethyl)-D-arabino-3-heptulofuranosonic acid To a stirred solution of 4.07 g of 2-deoxy-2,2-difluoro-4,5,7-tris-O-(phenylmethyl)-D-arabino-3-heptulofuranosonic acid, ethyl ester in 75 ml of ethanol was added 15 ml of 1N sodium hydroxide. After 60 minutes at 25° C., the mixture was acidified with carbon dioxide and concentrated. The residue was stirred with ether and water and acidified with hydrochloric acid. The ether layer was washed with water and brine, dried, and concentrated to give a colorless oil, IR 1770 cm$^{-1}$ (CF$_2$COOH).

EXAMPLE 64

1-Deoxy-1,1-difluoro-3,4,6-tris-O-(phenylmethyl)-D-fructofuranose

A stirred solution of 2.57 g of 2-deoxy-2,2-difluoro-4,5,7-tris-O-(phenylmethyl)-D-arabino-3-heptulofuranosonic acid in 25 ml of 2,6-lutidine was refluxed for 2 hours and then concentrated. The residue was subjected to column chromatography on silica gel to give an oil, CMR δ 113.1 (triplet, J=247Hz, $\underline{C}F_2$).

EXAMPLE 65

1-Deoxy-1,1-difluoro-3,4-bis-O-(phenylmethyl)-D-fructofuranose, diacetate

To a stirred solution of 0.88 g of 1-deoxy-1,1-difluoro-3,4,6-tris-O-(phenylmethyl)-D-fructofuranose in 3.7 ml of acetic anhydride was added 0.34 ml of boron trifluoride-etherate at 0° C.. After 90 minutes at 0° C., the solution was diluted with ether and stirred with sodium bicarbonate solution. The organic layer was washed with water and brine, dried, and concentrated. The residue was subjected to column chromatography on silica gel to give an oil, CMR δ 111.3 (triplet, J=249 Hz $\underline{C}F_2$ of minor anomer) and 111.9 (triplet, J=248 Hz, $\underline{C}F_2$ of major anomer).

EXAMPLE 66

1-Deoxy-1,1-difluoro-3.4-bis-O-(phenylmethyl)-D-fructofuranose

To a stirred solution of 5.77 q of 1-deoxy-1,1-difluoro-3,4-bis-O-(phenylmethyl)-D-fruotofuranose, diacetate in 37 ml of methanol was added 2.0 g of sodium methoxide. The resulting solution was stirred at 25° C. for 45 minutes, acidified with acetic acid, and partitioned with ethyl acetate-brine. The organic layer was dried and concentrated to give an oil, CMR δ 95.1 (triplet, $\underline{C}F_2$ of minor anomer) and 99.1 triplet, $\underline{C}F_2$ of major anomer).

EXAMPLE 67

1-Deoxy-1,1-difluoro-3,4-bis-O-(phenylmethyl)-D-fructofuranose, 6-(diphenyl phosohate)

To a stirred solution of 1.90 g of 1-deoxy-1,1-difluoro-3,4-bis-O-(phenylmethyl)-D-fructofuranose in 15 ml of pyridine at 0° C. was added 2.6 ml of diphenylphosphoryl chloride. After 2 hours the solution was treated with 3.0 ml of water, stirred at 25° C. for 45 minutes, and partitioned with ether-water. The organic layer was washed with brine, dried and concentrated. The residue was subjected to column chromatography on silica gel to give a syrup, CMR δ 67.6 (doublet, J=5.5 Hz, $\underline{C}H_2OP$).

EXAMPLE 68

1-Deoxy-1.1-difluoro-3,4-bis-O-(phenylmethyl)-D-fructofuranose, 2,6-bis(diphenyl phosphate), β-anomer To a stirred solution of 0.78 g of 1-deoxy-1,1-difluoro-3,4-bis-O-(phenylmethyl)-D-fructofuranose, 6-(diphenyl phosphate) and 0.38 g of dimethylaminopyridine in 6.4 ml of dichloromethane and 1.3 ml of pyridine was added 1.6 ml of diphenylphosphoryl chloride at 25° C. The mixture was stirred for 24 hours, cooled to 0° C., treated with 0.29 ml of water, stirred at 25° C. for 15 minutes, and partitioned with dichloromethane water. The organic layer was washed successively with water, cold dilute hydrochloric acid, sodium bicarbonate solution, and water, dried and concentrated. The residue was subjected to column chromatography on silica gel (dichloromethane-ether) to give the mobile β-anomer, CMR δ 104.5 (doublet of triplets, anomeric carbon).

EXAMPLE 69

1-Deoxy-1,1-difluoro-3,4-bis-O-(phenylmethyl)-D-fructofuranose, 2,6-bis(diphenyl phosohate), α-anomer In the manner of Example 68, treatment of 1-deoxy-1,1-difluoro-3,4-bis-O-(phenylmethyl)-D-fructofuranose, 6-(diphenyl phosphate) with diphenylphosphoryl chloride in the presence of dimethylaminopyridine followed by chromatography on silica gel gave the polar α-anomer as a syrup, CMR δ 106.7 (doublet of triplets, anomeric carbon).

EXAMPLE 70

1-Deoxy-1,1-difluoro-D-fructofuranose, 2,6-bis(dihydrogen phosphate), β-anomer, disodium salt A mixture of 0.14 g of 1-deoxy-1,1-difluoro-3,4-bis-O-(phenylmethyl)-D-fructofuranose, 2,6-bis(diphenyl phosphate), β-anomer, 0.12 g of 20% palladium hydroxide on carbon, and 15 ml of methanol was hydrogenated on a Parr shaker at 60 psi and 25° C. for 6.5 hours. The catalyst was filtered off under argon, and the filtrate was treated with 85 mg of platinum oxide. The mixture was hydrogenated on a Parr shaker at 60 psi and 25° C. for 16 hours and filtered. The filtrate was concentrated and the residue was partitioned with water-dichloromethane. The aqueous phase was treated with 7.0 ml of 0.05M sodium bicarbonate solution and concentrated to give a white foam, CMR δ 99.3 (doublet of triplets, anomeric carbon).

EXAMPLE 71

1-Deoxy-1,1-difluoro-D-fructofuranose. 2,6-bis(dihydrogen phosphate), α-anomer, disodium salt In the manner of Example 70, 1-deoxy-1,1-difluoro-3,4-bis-O-(phenylmethyl)-D-fructofuranose, bis(diphenyl phosphate), α-anomer, was hydrogenated successively in the presence of palladium hydroxide on carbon in methanol and platinum in methanol. After filtration of catalyst, concentration of filtrate, and treatment of the aqueous solution with 0.05M sodium bicarbonate, the title compound was obtained as colorless glass, CMR δ 100.8 (triplet, anomeric carbon)

EXAMPLES 72–73

Following the procedure of Example 70 and using the indicated starting materials, the products of Examples 72–73, shown below, are prepared.

| Example | Starting Material From Example | Product |
|---|---|---|
| 72 | 61 | 2-Deoxy-2,2-difluoro-D-arabino-3-heptulofuranosonic acid, ethyl ester-, 3,7-bis(dihydrogen phosphate), β-anomer, disodium salt |
| 73 | 62 | 2-Deoxy-2,2-difluoro-D-arabino-3-heptulofuranosonic acid, ethyl ester-, 3,7-bis(dihydrogen phosphate), α-anomer, disodium salt |

EXAMPLES 74–75

Using the indicated starting materials and first treating with sodium borohydride in ethanol and then following the procedure of Example 70. the products of Example 74 and 75, shown below, are prepared.

| Example | Starting Material From Example | Product |
|---|---|---|
| 74 | 61 | 2-Deoxy-2,2-difluoro-D-arabino-3-heptulofuranose, 3,7-bis(dihydrogen phosphate), β-anomer, disodium salt |
| 75 | 62 | 2-Deoxy-2,2-difluoro-D-arabino-3-heptulofuranose, 3,7-bis(dihydrogen phosphate), α-anomer, disodium salt |

EXAMPLE 76

1-Deoxy-1,1-difluoro-3,4-bis-O-(phenylmethyl)-D-fructofuranose, 2,6-bis(phenylmethyl phosphate), β-anomer To a stirred solution of 1.66 g of 1-deoxy-1,1-difluoro-3,4-bis-O-(phenylmethyl)-D-fructofuranose in 10 ml of tetrahydrofuran at 31 -78° C. was added 3.49 ml 2.5M n-butyllithium in hexane dropwise. After 5 minutes, a solution of 7.05g of tetrabenzyl pyrophosphate in 12 ml of tetrahydrofuran was added dropwise. After 5 minutes at −78° C., the solution was warmed to 0° C. After 60 minutes at 0° C., the solution was warmed to 25° C.. After 30 minutes at 25° C., the solution was cooled to 0° C. and treated dropwise with 4.4 ml of 1N sodium hydroxide, warmed to 25° C., and adjusted to pH above 10 with additional sodium hydroxide. The mixture was partioned with 2:1 ether-hexane and water. The organic layer was washed sequentially with water, sodium bicarbonate solution, water and brine; dried; and concentrated. The residue was subjected to chromatography on silica gel to give the mobile β-anomer, CMR δ 103.4 (doublet of triplets, anomeric carbon).

EXAMPLE 77

1-Deoxy-1,1-difluoro-3,4-bis-O-(phenylmethyl)-D-fructofuranose, 2,6-bis(phenylmethyl phosphate), α-anomer In the manner of Example 76, treatment of 1-deoxy-1,1-difluoro-3,4-bis-O-(phenylmethyl)-D-fructofuranose with n-butyllithium followed by treatment with tetrabenzyl phosphate and chromatography of the product mixture gave the polar α-anomer, CMR δ 106.0 (doublet of triplets, anomeric carbon).

EXAMPLE 78

1-Deoxy-1,1-difluoro-D-fructofuranose, 2,6-bis(dihydrogen phosohate), β-anomer, tetrasodium salt A mixture of 319 mg of 1-deoxy-1,1-difluoro-3,4-bis-O-(phenylmethyl)-D-fructofuranose, 2,6-bis (phenylmethyl phosphate), β-anomer, 35 mg of 20% palladium hydroxide on carbon and 20 ml of methanol was hydrogenated on a Parr shaker at 60 psi and 25° C. for 3 hours The mixture was filtered, and the filtrate was treated with 2.8 ml of 0.5M sodium bicarbonate. After extraction with dichloromethane, the aqueous solution was filtered and evaporated to give a white foam, CMR δ 101.6 (multiplet, anomeric carbon).

EXAMPLE 79

1,1-difluoro-D-fructofuranose, 2,6-bis(dihydrogen phosphate), α-anomer, tetrasodium salt In the manner of Example 78, hydrogenation of 1-deoxy-1,1-difluoro-3,4-bis-O-(phenylmethyl)-D-fructofuranose, 2,6-bis(phenylmethyl phosphate), α-anomer in the presence of 20% palladium hydroxide in methanol, followed by treatment with sodium bicarbonate gave the title compound as a white solid, CMR δ 105.0 (multiplet, anomeric carbon).

EXAMPLE 80

1-Deoxy-1,1-difluoro-3,4-bis-O-(phenylmethyl)-D-fructofuranose, 6-[2-methoxy-3-(hexadecyloxy)propyl phenyl phosohate A solution of 0.96 mmol of 1-deoxy-1,1-difluoro-3,4-bis-O-(phenylmethyl)-D-fructofuranose in 400 μl dry pyridine was added to a freshly prepared solution of 1.02 mmol of 2-methoxy-3-(hexadecyloxy)propyl phenyl chlorophosphate (prepared according to the references in Table II) in 4.0 ml dichloromethane at room temperature and the resulting mixture was stirred overnight under argon atmosphere. The mixture was treated with 100 μl of water and stirred for an additional hour. Work-up, following the procedure of Example 4, afforded an oil which was purified by flash chromatography, by elution with 1.5% methanol in dichloromethane. The fractions were evaporated giving 53% yield of the desired product.

EXAMPLE 81

1-Deoxy-1,1-difluoro-D-fructofuranose, 6-[2-methoxy-3-(hexadecyloxy)propyl phenyl phosphate]

A 410 mg portion of 1-deoxy-1,1-difluoro-3,4-bis-O-(phenylmethyl)-D-fructofuranose, 6-[2-methoxy-3-(hexadecyloxy)propyl phenyl phosphate] was dissolved in 22 ml methanol and 3 ml ethyl acetate and hydrogenated over 20% palladium hydroxide on carbon at 70 psi for 7 hours. Filtration and evaporation of the solvent gave an oil which was purified by chromatography, by elution with 4% methanol in dichloromethane. Fractions containing the desired material were evaporated to give 71% yield of the product.

EXAMPLE 82

1-Deoxy-1,1-difluoro-D-fructofuranose, 6-[2-methoxy-3-(hexadecyloxy)propyl hydrogen phosphate A solution of 210 mg of 1-deoxy-1,1-difluoro-D-fructofuranose, 6-[2-methoxy-3-(hexadecyloxy)propyl phenyl phosphate in 20 ml of methanol was hydrogenated at 60 psi over platinum oxide, following the procedure of Example 5. Evaporation afforded a quantitative yield of the desired product in the form of a wax.

EXAMPLE 83

1-Deoxy-1,1-difluoro-3,4-bis-O-(phenylmethyl)-D-fructofuranose, 6-(2-hydroxy-1,3,2-dioxaphosphorinane 2-oxide)

To a solution of 1.0 mmol of 1-deoxy-1,1-difluoro-3,4-bis-O-(phenylmethyl)-D-fructofuranose in 800 μl dry pyridine was added 1.1 mmol of 2-chloro-1,3,2-dioxaphosphacyclohexane 2-oxide (see the references to Table II) at 0° C. under argon. The resulting mixture was allowed to warm up slowly to room temperature and was stirred overnight. The mixture was treated with a few drops of water and stirred for 15 minutes. Work-up, following the procedure of Example 4, afforded an oil which was purified by flash chromatography, then by elution with 1.5:1.0 ethyl acetate:hexane solution. The fractions were evaporated, giving 80% yield of the desired product.

EXAMPLE 84

1-Deoxy-1,1-Difluoro-D-fructofuranose, 6-(2-hydroxy-1,3,2-dioxaphosphorinane 2-oxide)

A 240 mg portion of 1-deoxy-1,1-difluoro-3, 4-bis-O-(phenylmethyl)-D-fructofuranose, 6-(2-hydroxy-1,3,2-dioxaphosphorinane 2-oxide) was dissolved in 25 ml methanol and hydrogenated over 250 mg of 20% palladium hydroxide on carbon at 60 psi for 6 hours. Filtration and evaporation of the solvent gave 91% of the desired product.

EXAMPLE 85

1-Deoxy-1,1-difluoro-D-fructofuranose, 6-(dihydrogen phosphate), sodium salt

A mixture of 0.61 g of 1-deoxy-1,1-difluoro-3, 4-bis-O-(phenylmethyl)-D-fructofuranose, 6-(diphenyl phosphate) [prepared in accordance with Ex. 67], 0.35 g of 20% palladium hydroxide on carbon, and 100 ml of methanol was hydrogenated on a Parr shaker at 60 psi and 25° for 6.5 hours. After filtration of the catalyst, the filtrate was hydrogenated with platinum on a Parr shaker at 60 psi and 25° for 16 hours and filtered. The filtrate was concentrated, and the residue was partitioned with water and dichloromethane. The aqueous layer was treated with 2.0 ml of 0.5M sodium bicarbonate and evaporated to give a colorless foam, CMR δ 98.8 and 102.2 (triplets, J=24 Hz, β- and α-anomeric carbons).

EXAMPLE 86

2-Deoxy-2,2-difluoro-D-arabino-3-heptulofuranosonic acid, 7-(dihydrogen phosphate), trisodium salt In the manner of Examples 3 and 5, a 50 mg portion of 2-deoxy-2,2-difluoro-4,5-bis-O-phenylmethyl)-D-arabino-3-heptulofuranosonic acid, ethyl ester, 7-(diphenylphosphate) was hydrogenated successively in the presence of palladium hydroxide on carbon in methanol and platinum in methanol. After filtration of catalyst, treatment with 0.44·ml of 0.5M sodium bicarbonate solution, evaporation, and partition of the residue with water and dischloromethane, the aqueous solution was concentrated to give a colorless foam, CMR δ 100.1 (triplet, J=27 Hz, anomeric carbon).

EXAMPLE 87

2-Deoxy-2-fluoro-4,5,7-tris-O-(phenylmethyl)-D-arabino-3-heptulofuranosonic acid, ethyl ester To a stirred mixture of 2.88 g of zinc dust, 8.37 of 2,3,5-tris-O-(phenylmethyl)-D-arabinonic acid-gamma-lactone (see Example 57), and 90 ml of tetrahydrofuran was added a solution of 7.32 g of ethyl bromofluoroacetate in 10 ml of tetrahydrofuran during 45 minutes at 25°. After the addition, the mixture was refluxed for 16 hours, cooled, and partitioned with ether and 0.5M hydrochloric acid. The organic layer was washed successively with water, sodium bicarbonate solution, water, and brine dried; and concentrated. The crude product was purified by column chromatography on silica gel to give an oil, CMR δ 166–168 (four doublets for COOEt of four diastereomers).

EXAMPLE 88

2-Deoxy-2-fluoro-4,5,7-tris-O-(phenylmethyl-D-arabino-3-heptulofuranosonic acid

In the manner of Example 63, treatment of 0.13 g 2-deoxy-2-fluoro-4,5,7-tris-O-(phenylmethyl)-D-arabino-3-heptulofuranosonic acid, ethyl ester with 0.5 ml of 1N sodium hydroxide in 2.5 ml of ethanol gave a colorless oil, IR 1760 cm$^{-1}$ (CFHCOOH).

EXAMPLE 89

1-Deoxy-1-fluoro-3,4,6-tris-O-(phenylmethyl)-D-fructofuranose

In the manner of Example 64, decarboxylation of 0.12 g 2-deoxy-2-fluoro-4,5,7-tris-O-(phenylmethyl)-D-arabino-3-heptulofuranosonic acid in 2.5 ml of refluxing 2,6-lutidine afforded the desired compound as an oil, CMR δ 101.1 and 104.6 (doublets, J=21 Hz, β-and α-anomeric carbons).

EXAMPLE 90

1-Deoxy-1-fluoro-3,4-bis-O-(phenylmethyl-D-fructofuranose, diacetate

In the manner of Example 65, treatment of 8.31 g of 1-deoxy-1-fluoro-3,4,6-tris-O-(phenylmethyl)-D-fructofuranose in 37 ml of acetic anhydride with 3.4 ml of boron trifluoride etherate followed by work-up and purification gave an oil, CMR δ 6 105.2 and 108.6 (doublets, J=21 Hz, anomeric carbons).

EXAMPLE 91

1-Deoxy-1-fluoro-3,4-bis-O-(phenylmethyl)-D-fructofuranose

In the manner of Example 66, treatment of 4.2 g 1-deoxy-1-fluoro-3,4-bis-O-(phenylmethyl)-D-fructofuranose, diacetate with 47 ml of 1N sodium methoxide in methanol followed by workup and purification gave an oil, CMR δ 100.5 and 104.4 (doublets, J=20 Hz, β- and α-anomeric carbons).

EXAMPLE 92

1-Deoxy-1-fluoro-3,4-bis-O-(phenylmethyl)-D-fructofuranose, 6-(diphenyl phosphate)

In the manner of Example 67, treatment of 0.59 g 1-deoxy-1-fluoro-3,4-bis-O-(phenylmethyl)-D-fructofuranose with 0.84 ml of diphenyl phosphorochloridate in 4.9 ml of pyridine followed by work-up and chromatography gave an oil, CMR δ 101.7 and 104.9 (doublets, J-21 Hz, β- and α-anomeric carbons)

EXAMPLE 93

1-Deoxy-1-fluoro-D-fructofuranose, 6-(dihydrogen phosphate), disodium salt

In the manner of Example 85, 0.68 g of 1-deoxy-1-fluoro-3,4-bis-O-(phenylmethyl)-D-fructofuranose, 6-diphenyl phosphate) was hydrogenated successively in the presence of palladium hydroxide on carbon in methanol and platinum and methanol. After treatment with sodium bicarbonate and work-up the product was obtained as a white foam, CMR δ 102.5 and 105.7 (doublets, J=20 Hz, β- and α-anomeric carbons).

EXAMPLE 94

2-Deoxy-2,2-difluoro-D-arabino-3-heptulofuranose, 7-(dihydrogen phosphate), disodium salt In the manner of Example 74, 2-deoxy-2,2-difluoro-4,5-bis-O-(phenylmethyl)-D-arabino-3-heptulofuranosonic acid, ethyl ester, 7-(diphenyl phosphate) is treated first with sodium borohydride in ethanol and then following the procedure of Example 70 to give the desired compound.

EXAMPLE 95

1-Deoxy-1-(methylsulfinyl)-1-methylthio)-3,4,6-tris-O-(phenylmethyl)-D-fructofuranose To a stirred solution of 28.7 g of methyl (methylthiomethyl) sulfoxide in 275 ml of tetrahydrofuran was added 88 ml of 2.5M n-butyllithium during 15 minutes at −25°. After warming to 15°, the solution was cooled to −78° and treated during 5 minutes with a solution of 41.8 g of 2,3,5-tris-O-(phenylmethyl)-D-arabinonic acid-gamma-lactone [see Example 57] in 125 ml of tetrahydrofuran. After 5 minutes, the solution was warmed to −10°, stirred for 10 minutes, and then cooled to −78° and treated with 20 ml of acetic acid. The resulting mixture was partitioned with water and 1:1 ether-hexane. The organic layer was washed successively with water, sodium bicarbonate solution, water and brine; dried; and concentrated to give an oil, CMR δ 15.6 and 36.6 (singlets, CH$_3$S and CH$_3$SO of major diastereomer).

EXAMPLE 96

3,4,6-Tris-O-(phenylmethyl)-D-fructofuranonic acid, methyl ester

A mixture of 27.1 g of 1-deoxy-1-(methylsulfinyl)-1-(methylthio)-3,4,6-tris-O-(phenylmethyl)-D-fructofuranose, 20.2 g of cupric chloride, 23.9 g of cupric oxide, and 300 ml of methanol was stirred at reflux temperature for 5 hours. After evaporation of methanol, the residue was stirred with dichloromethane and filtered through Celite. The filtrate was washed with water and sodium bicarbonate solution, dried, filtered, and concentrated. The residue was subjected to column chromatography on silica gel to give an oil, CMR δ 53.2 (CH$_3$OCO).

EXAMPLE 97

3.4Bis-O-(phenylmethyl)-D-arabinohexulofuranosonic acid, methyl ester, diacetate To a stirred solution of 9.57 g of 3,4,6-tris-O-(phenylmethyl)-D-fructofuranonic acid, methyl ester in 40 ml of acetic anhydride was added 3.7 ml of boron trifluoride etherate dropwise at 0°. After 1.5 hours at 0°, the solution was diluted with ether and stirred at 0° for 15 minutes with 10 ml of saturated sodium bicarbonate solution. The organic layer was washed with water and brine, dried, and concentrated. The residue was subjected to chromatography on silica gel to give an oil, CMR δ 101.3 and 105.2 (singlets, anomeric carbon of β- and α-anomers).

EXAMPLE 98

3,4-Bis-O-(phenylmethyl)-D-arabino-2-hexulofuranosonic acid, methyl ester

A solution of 4.25 g of 3,4-bis-O-(phenylmethyl)-alpha-D-arabino-hexulofuranosonic acid, methyl ester, diacetate in 45 ml of 1.0M sodium methoxide in methanol was stirred at 25° for 20 minutes, treated with 4.1 ml of acetic acid, and concentrated. The residue was partitioned with ethyl acetate and water. The organic layer was washed with water and brine, dried, and concentrated. The residue was subjected to chromatography on silica gel to give an oil, CMR δ 53.3 ($\underline{C}H_3OCO$).

EXAMPLE 99

3,4-Bis-O-(phenylmethyl)-D-arabino-2-hexulofuranosonic acid, methyl ester, 6-(diphenyl phosphate)

To a stirred solution of 0.78 g of 3,4-bis-O-(phenylmethyl)-D-arabino-2-hexulofuranosonic acid, methyl ester in 6.0 ml of pyridine at 0° was added 1.04 ml of diphenylphosphorochloridate dropwise. After 2 hours the solution was warmed to 25° and then stirred at 25° with 1.2 ml of water for 45 minutes. The solution was partitioned with ether and water. The organic layer was washed with water and brine, dried, and concentrated. The residue was subjected to column chromatography on silica gel to give an oil, CMR δ 99.2 and 103.2 (singlets, anomeric carbon of β- and α-anomers).

EXAMPLE 100

D-Arabino-2-hexulofuranosonic acid. 6-(dihydrogen phosphate), disodium salt

A mixture of 0.57 g of 3,4-bis-O-(phenylmethyl-D-arabino-2-hexulofuranosonic acid, methyl ester, 6-(diphenyl phosphate), 0.30 g of 20% palladium hydroxide on carbon and 75 ml of methanol was hydrogenated on a Parr shaker at 60 psi and 25° for 7 hours. The catalyst was filtered off under argon, and the filtrate was treated with 0.20 g of platinum oxide. The mixture was hydrogenated on a Parr shaker at 60 psi and 25° for 16 hours and filtered. The filtrate was treated with 3.68 ml of 0.5M sodium bicarbonate and concentrated. The residue was partitioned with water and dichloromethane. The aqueous phase was concentrated to give a colorless glass, CMR δ 102.5 (anomeric carbon) and 178.2 (carboxylate carbon).

We claim:

1. A compound selected from those of the formula:

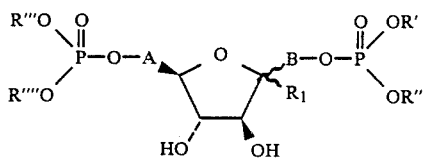

wherein A and B are selected independently of each other from the group consisting of $C_1$ to $C_4$ alkylene and $C_2$ to $C_4$ hydroxyalkylene; $R_1$ is selected from the group consisting of hydrogen, $C_1$ to $C_4$ alkyl, $C_1$ to $C_4$ hydroxyalkyl, $C_2$ to $C_4$ dihydroxyalkyl, $C_3$ or $C_4$ trihydroxyalkyl and $C_4$ tetrahydroxyalkyl; R', R", R'" and R"" are selected independently from the group consisting of hydrogen, $C_1$ to $C_{18}$ alkyl, $C_3$ to $C_6$ cycloalkyl, phenyl, isoalkyl ($C_3$–$C_8$), $Cl_3CCH_2$—, $CH_2=CHCH_2$—, $ZCH_2CH_2$— [where Z is $SO_2R_2$, $SR_2$, $OR_2$ or $Si(R_2)_3$, and $R_2$ is alkyl ($C_1$–$C_3$)],

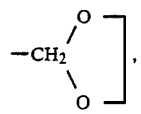

halo,

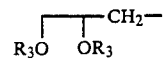

[where $R_3$ is hydrogen, alkyl ($C_1$–$C_{18}$) and $R_3$-$R_3$ is alkylene or acetal],

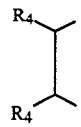

(where $R_4$ is hydrogen or methyl),

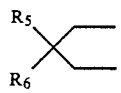

where when $R_5=R_6$, they are both hydrogen, fluoro or alkyl ($C_1$–$C_4$), $R_5$=hydrogen, $R_6$=fluoro, hydroxy or $OR_7$ [where $R_7$=alkyl ($C_1$–$C_6$), cycloalkyl ($C_3$–$C_6$) or aryl]],

[where $R_8$=hydrogen or alkyl ($C_1$–$C_{18}$)],

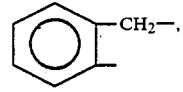

phenylmethyl, substituted phenylmethyl wherein the substituents are selected from alkyl ($C_1$–$C_{18}$), alkoxy ($C_1$–$C_6$), $NO_2$ and halogen, and mono- and disubstituted phenyl wherein the substituents are selected from alkyl ($C_1$–$C_{18}$), alkoxy ($C_1$–$C_6$), $NO_2$ and halogen; with the proviso that when A and B are both —$CH_2$—, then $R_1$ may not be hydrogen; and, when any one or more of R', R", R'" or R"" are hydrogen, the pharmacologically acceptable salts thereof.

2. The compound according to claim 1, 3,6-anhydro-2-deoxy-D-gluco-heptitol, 1,7-bis(diphenyl phosphate).

3. The compound according to claim 1, 3,6-anhydro-2-deoxy-D-gluco-heptitol, 1,7-bis(diethyl phosphate).

4. The compound according to claim 1, 3,6-anhydro-2-deoxy-D-manno-heptitol, 1,7-bis(diphenyl phosphate).

5. The compound according to claim 1, 3,6-anhydro-2-deoxy-D-manno-heptitol, 1,7-bis(diethyl phosphate).

6. The compound according to claim 1, 4,7-anhydro-2,3-dideoxy-D-gluco-octitol, 1,8-bis(diphenyl phosphate).

7. The compound according to claim 1, 4,7-anhydro-2,3-dideoxy-D-gluco-octitol, 1,8-bis(diethyl phosphate).

8. The compound according to claim 1, 4,7-anhydro-2,3-dideoxy-D-manno-octitol, 1,8-bis(diphenyl phosphate).

9. The compound according to claim 1, 4,7-anhydro-2,3-dideoxy-D-manno-octitol, 1,8-bis(diethyl phosphate).

10. The compound according to claim 1, 2,5-anhydro-2-C-(hydroxymethyl)-D-glucitol, 1,6-bis(diphenyl phosphate).

11. The compound according to claim 1, 2,5-anhydro-2-C-(hydroxymethyl)-D-glucitol, 1,6-bis(diethyl phosphate).

12. The compound according to claim 1, 2,5-anhydro-2-C-[[diphenoxyphosphinyl)oxy]methyl]-D-glucitol, 6-(diphenyl phosphate).

13. The compound according to claim 1, 2,5-anhydro-2-C-[[(diphenoxyphosphinyl)oxy]methyl]-D-glucitol, 6-(diethyl phosphate).

14. The compound according to claim 1, 3,6-anhydro-2-deoxy-D-gluco-heptitol, 1,7-bis(dihydrogen phosphate).

15. The compound according to claim 1, 3,6-anhydro-2-deoxy-D-manno-heptitol, 1,7-bis(dihydrogen phosphate).

16. The compound according to claim 1, 4,7-anhydro-2,3-dideoxy-D-gluco-octitol, 1,8-bis(dihydrogen phosphate).

17. The compound according to claim 1, 4,7-anhydro-2,3-dideoxy-D-manno-octitol, 1,8-bis(dihydrogen phosphate).

18. The compound according to claim 1, 2,5-anhydro-D-glycero-D-manno-heptitol, 1,7-bis(dihydrogen phosphate).

19. The compound according to claim 1, 2,5-anhydro-2-C-(hydroxymethyl)-D-glucitol, 1,6-bis(dihydrogen phosphate).

20. The compound according to claim 1, 2,5-anhydro-2-C-[(phosphonooxy)methyl]-D-glucitol, 6-(dihydrogen phosphate).

21. The compound according to claim 1, 3,6-anhydro-2-deoxy-3-C-(hydroxymethyl)-D-manno-heptitol, 1,7-bis(dihydrogen phosphate).

22. A compound selected from those of the formula:

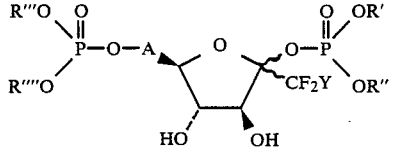

wherein A is selected from the group consisting of $C_1$ to $C_4$ alkylene and $C_2$ to $C_4$ hydroxyalkylene; R', R'', R''' and R'''' are selected independently from the group consisting of hydrogen, $C_1$ to $C_{18}$ alkyl, $C_3$ to $C_6$ cycloalkyl, phenyl, isoalkyl ($C_3$-$C_8$), $Cl_3CCH_2$—, $CH_2$=$CHCH_2$—, $ZCH_2CH_2$— [where Z is $SO_2R_2$, $SR_2$, $OR_2$ or $Si(R_2)_3$, and $R_2$ is alkyl ($C_1$-$C_3$)],

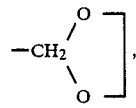

halo,

where $R_3$ is hydrogen, alkyl ($C_1$-$C_{18}$) and $R_3$-$R_3$ is alkylene or acetal],

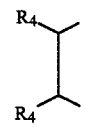

(where $R_4$ is hydrogen or methyl),

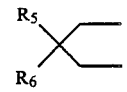

where when $R_5$=$R_6$ they are both hydrogen, fluoro or alkyl ($C_1$-$C_4$), $R_5$=hydrogen, $R_6$=fluoro, hydroxy or $OR_7$ [where $R_7$=alkyl ($C_1$-$C_6$), cycloalkyl ($C_3$-$C_6$) or aryl]],

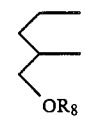

[where $R_8$=hydrogen or alkyl ($C_1$-$C_{18}$)],

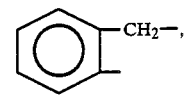

phenylmethyl, substituted phenylmethyl wherein the substituents are selected from alkyl ($C_1$-$C_{18}$), alkoxy ($C_1$-$C_6$), $NO_2$ and halogen, and mono- and disubstituted phenyl wherein the substituents are selected from alkyl ($C_1$-$C_{18}$), alkoxy ($C_1$-$C_6$), $NO_2$ and halogen; Y is selected from the group consisting of hydrogen, $COOR_9$ and $CH_2OH$, where $R_9$ is hydrogen or a salt thereof, or alkyl ($C_1$-$C_6$).

23. The compound according to claim 22, 2-deoxy-2,2-difluoro-D-arabino-3-heptulofuranosonic acid, ethyl ester-, 3,7-bis(dihydrogen phosphate), β-anomer, disodium salt.

24. The compound according to claim 22, 2-deoxy-2,2-difluoro-D-arabino-3-heptulofuranosonic acid, ethyl ester-, 3,7-bis(dihydrogen phosphate), α-anomer, disodium salt.

25. The compound according to claim 22, 1-deoxy-1,1-difluoro-D-fructofuranose, 2,6-bis(dihydrogen phosphate), β-anomer, disodium salt.

26. The compound according to claim 22, 1-deoxy-1,1-difluoro-D-fructofuranose, 2,6-bis(dihydrogen phosphate), α-anomer, disodium salt.

27. The compound according to claim 22, 1-deoxy-1,1-difluoro-D-fructofuranose, 2,6-bis(dihydrogen phosphate), β-anomer, tetrasodium salt.

28. The compound according to claim 22, 1-deoxy-1,1-difluoro-D-fructofuranose, 2,6-bis(dihydrogen phosphate), α-anomer, tetrasodium salt.

29. The compound according to claim 22, 2-deoxy-2,2-difluoro-D-arabino-3-heptulofuranose, 3,7-bis(dihydrogen phosphate), β-anomer, disodium salt.

30. The compound according to claim 22, 2-deoxy-2,2-difluoro-D-arabino-3-heptulofuranose, 3,7-bis(dihydrogen phosphate), β-anomer, disodium salt.

31. A compound selected from those of the formula:

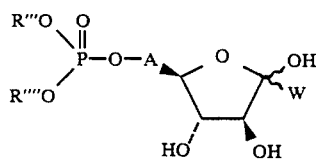

wherein A is selected from the group consisting of $C_1$ to $C_4$ alkylene and $C_2$ to $C_4$ hydroxyalkylene; R''' and R'''' are selected independently from the group consisting of hydrogen, $C_1$ to $C_{18}$ alkyl, $C_3$ to $C_6$ cycloalkyl, phenyl, isoalkyl ($D_3$-$C_8$), $Cl_3CCH_2$—, $CH_2$=$CHCH_2$—, $ZCH_2CH_2$— ]where Z is $SO_2R_2$, $SR_2$, $OR_2$or $Si(R_2)_3$, and $R_2$is alkyl ($C_1$-$C_3$)],

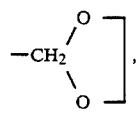

halo,

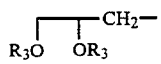

[where $R_3$ is hydrogen, alkyl ($C_1$-$C_{18}$) and $R_3$-$R_3$ is alkylene or acetal],

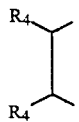

(where $R_4$ is hydrogen or methyl),

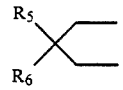

where when $R_5$=$R_6$ they are both hydrogen, fluoro or alkyl ($C_1$-$C_4$), $R_5$=hydrogen, $R_6$=fluoro, hydrogen or $OR_7$ [where $R_7$=alkyl ($C_1$-$C_6$), cycloalkyl ($C_3$-$C_6$) or aryl]],

[where $R_8$=hydrogen or alkyl ($C_1$-$C_{18}$)],

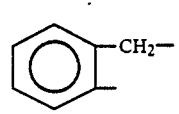

phenylmethyl, substituted phenylmethyl wherein the substituents are selected from alkyl ($C_1$-$C_{18}$), alkoxy ($C_1$-$C_6$), $NO_2$ and halogen, and mono and disubstituted phenyl wherein the substituents are selected from alkyl ($C_1$-$C_{18}$), alkoxy ($C_1$-$C_6$), $NO_2$ and halogen, —$CH_2CH_2N^+(CH_3)_3$,

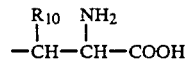

[where $R_{10}$ is hydrogen or $C_1$ to $C_3$ alkyl] and

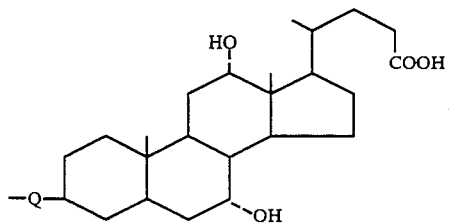

[where Q is a bond, —$(CH_2)_n$ or —$(CH_n$—O— and n=1–3]; and W is selected from the group consisting of —$CFH_2$, —$CF_2H$, —$CF_3$, —$CF_2CH_2OH$, —$CF_2COOH$, COOH, and —$COOCH_3$, and the pharmacologically acceptable salts thereof.

32. The compound according to claim 31, 1-deoxy-1,1-difluoro-D-fructofuranose, 6-[2-methoxy-3-(hexadecyloxyl)propyl hydrogen phosphate.

33. The compound according to claim 31, 1-deoxy-1,1-difluoro-D-fructofuranose, 6-(2-hydroxy-1,3,2-dioxaphosphorinane 2-oxide).

34. The compound according to claim 31, 1-deoxy-1,1-difluoro-D-fructofuranose, 6-(dihydrogen phosphate), sodium salt.

35. The compound according to claim 31, 2-deoxy-2,2-difluoro-D-arabino-3-heptulofuranosonic acid, 7-(dihydrogen phosphate), trisodium salt.

36. The compound according to claim 31, 1-deoxy-1-fluoro-D-fructofuranose, 6-(dihydrogen phosphate), disodium salt.

37. The compound according to claim 31, 2-deoxy-2,2-difluoro-D-arabino-3-heptulofuranose, 7-(dihydrogen phosphate), isodium salt.

38. The compound according to claim 31, D-arabino-2-hexulofuranosonic acid, 6-(dihydrogen phosphate), disodium salt.

39. A method of treating hyperglycemia in a mammal in need of such treatment which comprises administering to said mammal a therapeutically effective amount of a compound selected from those of claim 1, claim 22 or claim 31.

40. A pharmaceutical composition of matter which comprises a therapeutically effective amount of a compound selected from those of claim 1, claim 22 or claim 31 in association with a pharmaceutically acceptable carrier.

41. A method of increasing starch production and reducing root growth in plants which comprises administering to said plant an effective amount of a compound selected from those of claim 1, claim 22 or claim 31.

42. A method of treating diabetes in a mammal in need of such treatment which comprises administering to said mammal a therapeutically effective amount of a compound elected from those of claim 1, claim 22 or claim 31.

* * * * *